US010704096B2

(12) United States Patent
Hamm-Alvarez et al.

(10) Patent No.: US 10,704,096 B2
(45) Date of Patent: *Jul. 7, 2020

(54) BIOMARKERS FOR THE EARLY DETECTION OF AUTOIMMUNE DISEASES

(75) Inventors: Sarah Hamm-Alvarez, Los Angeles, CA (US); Kaijin Wu, Los Angeles, CA (US); Maria Charlotta Edman, Los Angeles, CA (US)

(73) Assignee: University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/382,286

(22) PCT Filed: Jul. 6, 2010

(86) PCT No.: PCT/US2010/041092
§ 371 (c)(1),
(2), (4) Date: Mar. 14, 2012

(87) PCT Pub. No.: WO2011/005779
PCT Pub. Date: Jan. 13, 2011

(65) Prior Publication Data
US 2012/0171221 A1  Jul. 5, 2012

Related U.S. Application Data

(60) Provisional application No. 61/223,692, filed on Jul. 7, 2009, provisional application No. 61/266,985, filed on Dec. 4, 2009, provisional application No. 61/328,168, filed on Apr. 26, 2010.

(51) Int. Cl.
C12Q 1/6883 (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
CPC ...... C07K 16/18; C07K 14/705; C07K 16/22; C07K 16/244; C07K 14/5437; C07K 14/7155; C07K 16/248; C07K 16/2866; C07K 2319/50
See application file for complete search history.

(56) References Cited

U.S. PATENT DOCUMENTS

| 5,006,310 | A | 4/1991 | Gin et al. | |
|---|---|---|---|---|
| 5,100,899 | A | 3/1992 | Calne | |
| 6,160,095 | A | 12/2000 | Chaudhary et al. | |
| 6,190,691 | B1 | 2/2001 | Mak | |
| 2004/0229863 | A1* | 11/2004 | Cummings et al. | 514/217.04 |
| 2007/0086979 | A1 | 4/2007 | Chevrier et al. | |
| 2009/0258828 | A1* | 10/2009 | Beuerman et al. | 514/12 |
| 2009/0263825 | A1* | 10/2009 | Castro | G01N 33/5432 435/7.1 |
| 2011/0224133 | A1 | 9/2011 | Jung et al. | |
| 2011/0257103 | A1 | 10/2011 | Hamm-Alvarez | |
| 2012/0183568 | A1 | 7/2012 | Hamm-Alvarez | |

FOREIGN PATENT DOCUMENTS

| CN | 1858059 A | 11/2006 | |
|---|---|---|---|
| WO | WO 2006/010041 A2 | 1/2006 | |
| WO | WO 2006062626 A1 * | 6/2006 | ........... G01N 33/558 |
| WO | WO-2006062626 A1 * | 6/2006 | ........... G01N 33/558 |
| WO | WO 2010/011952 | 1/2010 | |
| WO | WO-2011/005779 | 1/2011 | |
| WO | WO 2012/015836 | 2/2012 | |

OTHER PUBLICATIONS

Prince. Biomarkers for diagnosing and monitoring autoimmune disease. Biomarkers. 10 (Supplement 1):S44-S49, 2005.*
Gibson et al. Diagnostic and prognostic biomrker discovery strategies for autoimmune disorders. Journal of Proteomics. 73:1045-1060, 2010.*
Tektonidou et al. Validity of clinical associations of biomarkers in translational research studies: the case of systemic autoimmune disease. Arthritis Research and Therapy. 12:R179: 1-10, Sep. 2010).*
Wu et al. Altered expression of genes functioning in lipid homestasis is associated with lipid depostion in NOD mouse lacrimal gland. Experimental Eye Research. 89:319-322, Apr. 2, 2009.*
Li et al. Increased expression of cathepsins and their regulatory cytokines in the lacrimal gland of male NOD mouse. Investigative Ophthalmology and Visual Science. 49:E-abstract 425, Apr. 11, 2008.*
Li et al. Increased expression of cathepsins and their regulatory cytokines in the lacrimal gland of male NOD mouse. Investigative Ophthalmology and Visual Science. Apr. 11, 2008; 49:E-abstract 425.*

(Continued)

*Primary Examiner* — Vanessa L. Ford
*Assistant Examiner* — Sandra E Dillahunt
(74) *Attorney, Agent, or Firm* — Foley & Lardner LLP

(57) ABSTRACT

Provided are methods for aiding in diagnosing autoimmune diseases in a mammal, comprising contacting a sample of tear from the mammal with an antibody that specifically binds to a first polypeptide selected from the group Ctss, Ctsh, Ctsr, Ctsw, Ctsz, Ifng, Il16ra, Il10, Il10ra, Il15, Tnfa, Apo-F, or Lcn-2 or a second polypeptide selected from the group lactoperoxidase, lactoferrin or lysozyme under conditions favoring the formation of an antibody-polypeptide complex, and determining the amount of complex formed, wherein an increased formation of antibody-first-polypeptide complex or a decreased formation of antibody-second-polypeptide complex as compared to a suitable control, indicates a likely positive diagnosis of an autoimmune disease for the mammal, thereby aiding in the diagnosis. Methods of treating the autoimmune diseases are also provided.

15 Claims, 23 Drawing Sheets

(56) References Cited

OTHER PUBLICATIONS

Araki et al. Th1/Th2 cytokine levels in the tear fluid of patients with Sjogren's Syndrome. Investigative Ophthalmology and Visual Science. 2005; 46: E-abstract 4464.*

Araki et al. (Investigative Ophthalmology and Visual Science. 2005; 46: E-abstract 4464.*

Li et al. (Investigative Ophthalmology and Visual Science. Apr. 11, 2008; 49: E-abstract 425.*

Araki et al. Th1/Th2 Cytokine Levels in the Tear Fluid of Patients With Sjogren's Syndrome. Investigative Ophthalmology and Visual Science. 2005; 46: E-abstract 4464 (Year: 2005).*

Li et al. Increased Expression of Cathepsins and Their Regulatory Cytokines in the Lacrimal Gland of Male NOD Mouse. Investigative Ophthalmology and Visual Science, Apr. 11, 2008; 49: E-abstract 425 (Year: 2008).*

Wu et al., (2009) "Altered expression of genes functioning in lipid homeostasis is associated with lipid deposition in NOD mouse lacrimal gland," Experimental Eye Research 89(3): 319-332.

Azuma et al., (2002) "Identification of candidate genes for Sjögren's syndrome using MRL/lpr mouse model of Sjögren's syndrome and cDNA microarray analysis," Immunology Letters 81(3): 171-176.

Sohar et al., (2005) "Lysosomal enzyme activities: New potential markers for Sjögren's syndrome," Clinical Biochemistry 38(12): 1120-1126.

Kim et al., (2008) "Exogenous tumor necrosis factor α induces suppression of autoimmune arthritis," Arthritis Research & Therapy 10(1): 1-10.

Link et al., (2006) "Advances in cathepsin S inhibitor design," Current Opinion in Drug Discovery & Development 9(4): 471-482.

Taubert et al., (2002) "Expression of Cathepsin B, D and L Protein in Juvenile Idiopathic Arthritis," Autoimmunity 35(3): 221-224.

Centola et al., (2006) "Genome-scale Assessment of Molecular Pathology in Systemic Autoimmune Diseases using Microarray Technology: A Potential Breakthrough Diagnostic and Individualized Therapy-design Tool," Scandinavian Journal of Immunology 64(3): 236-242.

Flanagan et al., (2009) "Role of lactoferrin in the tear film," Biochimie 91(1): 35-43.

Caffery et al., (2008) "Tear Lipocalin and Lysozyme in Sjögren and Non-Sjögren Dry Eye," Optometry and Vision Science 85(8): 661-667.

Schenke-Layland et al., (2010) "Lymphocytic infiltration leads to degradation of lacrimal gland extracellular matrix structures in NOD mice exhibiting a Sjögren's syndrome-like exocrinopathy," Experimental Eye Research 90(2): 223-237.

International Search Report for PCT/US2010/041092, dated Jan. 20, 2011, 7 pages.

American Dental Association, "Potential Salivary Biomarkers Identified for Detecting Primary Sjögren's Syndrome," taken from www.ada.org/3142.aspx, printed on Apr. 25, 2012.

Barabino et al. (2004) "Animal Models of Dry Eye: A Critical Assessment of Opportunities and Limitations," Invest Ophthalmol Vis Sci. 45(6):1641-1646.

Flo et al. (2004) "Lipocalin 2 Mediates an Innate Immune Response to Bacterial Infection by Sequestrating Iron," Nature 432:917-921.

Franceschini et al. (2005) Abstract, "Anti-Ro/SSA and La/SSB antibodies," Autoimmunity 38 (1):55-63.

Ghibaudi et al. (2003) "Unraveling the Catalytic Mechanism of Lactoperoxidase and Myeloperoxidase," Eur J Biochem. 270:4403-4412.

Gupta et al. (2008) Abstract, "Cysteine Cathepsin S as an Immunomodulatory Target: Present and Future Trends," Expert Opin Ther Targets 12(3):291-299.

Hu et al. (2010) "Preclinical Validation of Salivary Biomarkers for Primary Sjögren's Syndrome," Arthritis Care & Research 62(11):1633-1638.

Hu et al. (2007) "Salivary Proteomic and Genomic Biomarkers for Primary Sjögren's Syndrome," Arthritis Rheum. 56(11):3588-3600.

Katunuma et al. (1999) "Structure Based Development of Novel Specific Inhibitors for Cathepsin L and Cathepsin S In Vitro and In Vivo," FEBS Letters 458:6-10.

Li et al. "Increased Expression of Cathepsins and Their Regulatory Cytokines in the Lacrimal Gland of Male NOD Mouse," Program No. 425, Session No. 122, presented at ARVO Annual Meeting, Fort Lauderdale, Florida, Apr. 27-May 1, 2008.

Liu et al. (2006) "Increased Serum Cathepsin S in Patients with Atherosclerosis and Diabetes," Atherosclerosis 186:411-419.

Meijer et al. (2007) "The Future of Biologic Agents in the Treatment of Sjögren's Syndrome," Clin Rev Allergy Immunol 32:292-297.

Nazmul-Hossain "Validation of Salivary-Biomarkers for Sjögren's Syndrome Detection in US population," International & American Association for Dental Research, presented on Mar. 19, 2011, San Diego Convention Center.

Nguyen et al. (2009) "Differential Gene Expression in the Salivary Gland During Development and Onset of Xerostomia in Sjögren's Syndrome-like Disease of the C57BL/6.NOD-Aec1Aec2 Mouse," Arthritis Res. Ther. 11(2)R56:1-16.

Nguyen et al. (2009) "Differential Gene Expressions in the Lacrimal Gland During Development and Onset of Keratoconjunctivitis Sicca in Sjögren's Syndrome (SJS)-like Disease of the C57BL/6.NOD-Aec1Aec2 Mouse," Exp Eye Res. 88:398-409.

Tomosugi et al. (2005) "Diagnostic Potential of Tear Proteomic Patterns in Sjögren's Syndrome," J. Proteome Res. 4(3):820-825.

Turk et al. (2001) "Lysosomal Cysteine Proteases: Facts and Opportunities," EMBO J. 20(17):4629-4633.

Weinberg (2007) Abstract, "Antibiotic Properties and Applications of Lactoferrin," Curr Pharm Des. 13(8):801-811.

Wu et al. (2010) "Gene Expression of Apolipoproteins in Human Lacrimal Gland," Abstract, Poster Session, Program No. 6240, Board No. D851.

Wu et al. "Genes Encoding Salivary Gland-Enriched Proteins Exhibit Increased Expression in Diseased Lacrimal Glands from Male NOD Mice," Program No. 2450, Session No. 312, presented at ARVO Annual Meeting, Fort Lauderdale, Florida, Apr. 27-May 1, 2008.

Zimecki et al. (2007) Abstract, "Milk-derived Proteins and Peptides of Potential Therapeutic and Nutritive Value," J. Exp Ther. Oncol. 6(2):89-106.

Zoukhri et al. (2002) "Role of Proinflammatory Cytokines in the Impaired Lacrimation Associated with Autoimmune Xerophthalmia," Invest Ophthalmol Vis Sci. 43(5):1429-1436.

U.S. Appl. No. 13/812,482, filed Jul. 26, 2011, Jung.

Database WPI Week 200751, 2007-514150.

Lee et al., "FLIP-mediated autophagy regulation in cell death control," Nature Cell Bilogy 11(11):1355-62 (2009).

Shintani et al., "Autophagy in health and disease: a double-edge sword," Science 306(5698):990-995,986 (2004).

Sir et al., "Autophagy in viral replication and pathogenesis," Molecules and Cells, pp. 1-7 http://www.springerlink.com/content/w118635146864815/fulltext.pdf (2010).

Ye et al., "Kaposi's sarcoma-associated herpes virus latent gene vFLIP inhibits viral lytic replication through NF-kappa B-mediated supression of the AP-1 pathway: a novel mechanism of virus control of latency," Journal of Virology 82(9): 4235-4249 (2008).

Alberts et al., Molecular Biology of the Cell, Third Edition, pp. 129-130 (1994).

Saegusa et al., "Cathepsin S inhibitor prevents autoantigen presentation and autoimmunity", The Journal of Clinical Investigation, 11(3): 361-369 (2002).

Small, et al., "The Emerging Relevance of the Cysteine Protease Cathepsin S in Disease" Clinical Rev Bone Miner Metab., 9:122-132 (2011).

U.S. Office Action for U.S. Appl. No. 12/931,601 dated Nov. 6, 2012.

U.S. Office Action for U.S. Appl. No. 13/324,963 dated Aug. 20, 2013.

U.S. Restriction Requirement for U.S. Appl. No. 13/324,963 dated Nov. 20, 2012.

Non-Final Office Action for U.S. Appl. No. 13/324,963 dated Aug. 20, 2014, 13 pages.

Advisory Action for U.S. Appl. No. 13/324,963 dated Apr. 15, 2014, 3 pages.

(56) References Cited

OTHER PUBLICATIONS

Final Office Action for U.S. Appl. No. 13/324,963, dated Jan. 8, 2014, 14 pages.
Restriction Requirement for U.S. Appl. No. 13/324,963, dated Jun. 10, 2013, 15 pages.
Final Office Action for U.S. Appl. No. 12/931,601, dated Sep. 5, 2013, 12 pages.
U.S. Appl. No. 12/931,601, filed Feb. 3, 2011, Hamm-Alvarez.
U.S. Appl. No. 13/324,963, filed Dec. 13, 2011, Hamm-Alvarez.
Benito, A.I. et al. (2001) "Sirolimus (Rapamycin) for the Treatment of Steroid-Refractory Acute Graft-Versus-Host Disease," Transplantation 72(12):1924-1929.
Fang, Y. et al. (2011) "Effect of Transgenic Overexpression of FLIP on Lymphocytes on Development and Resolution of Experiemental Autoimmune Thyroiditis," The American Journal of Pathology 179(3):1211-1220.
Fiore, D.C. et al. (2010) "Pain in the Quiet (Not Red) Eye," Am Fam Physician 82(1):69-73.
Jabs, D.A. et al. (2004) "Inflammatory Mediators in Autoimmune Lacrimal Gland Disease in MRL/Mpj Mice," Invest Ophthalmol Vis Sci. 45:2293-2298.
Öztürk, S. et al. (2012) "Cellular FLICE-like inhibitory proteins (c-FLIPs): Fine-tuners of life and death decisions," Experimental Cell Research 318:1324-1331.
Non-Final Office Action for U.S. Appl. No. 12/931,601, dated Nov. 24, 2014, 8 pages.
Non-Final Office Action for U.S. Appl. No. 12/931,601, dated Jul. 8, 2015, 8 pages.
Final Office Action for U.S. Appl. No. 13/324,963, dated Apr. 1, 2015, 13 pages.
U.S. Office Action dated Oct. 18, 2016, from U.S. Appl. No. 13/324,963.
Non-Final Office Action for U.S. Appl. No. 13/324,963, dated Jun. 1, 2016, 10 pages.
U.S. Notice of Allowance dated Nov. 9, 2016, from U.S. Appl. No. 13/324,963.
Non-Final Office Action on U.S. Appl. No. 12/931,601, dated Sep. 20, 2016, 10 pages.
Shah et al. "A rapamycin-binding protein polymer nanoparticle shows potent therapeutic activity in suppressing autoimmune dacryoadenitis in a mouse model Sjogren's syndrome," J Control Release, Nov. 10, 2013; 171(3): 269-79. Epub Jul. 25, 2013.
U.S. Notice of Allowance dated Apr. 17, 2017, from U.S. Appl. No. 12/931,601.
U.S. Office Action dated Aug. 11, 2017, from U.S. Appl. No. 15/598,216.
Notice of Allowance dated Jul. 19, 2018, from U.S. Appl. No. 15/451,214.
Keystone, "The utility of tumour necrosis factor blockade in orphan diseases," Ann Rheum Dis 63(Supp II): ii79-ii83 (2004).
Pajak B. et al. (2012), "Verapamil-induced autophagy-like process in colon adenocarcinoma COLO 205 cells; the ultrastructural studies", Pharmacol. Rep. 2012; 64:991-996.
Rubinsztein D. C. et al. (2012), "Autophagy modulation as a potential therapeutic target for diverse diseases", Nature Review, Drug Discovery 11(9):709-730, Sep. 2012.
Sada et al., "Biologic treatment in SS", Rheumatology, 2014.
Final Office Action in U.S. Appl. No. 12/931,601 dated Apr. 20, 2016.

\* cited by examiner

A

B

A

B

BIOMARKERS FOR THE EARLY DETECTION OF AUTOIMMUNE DISEASES

CROSS-REFERENCE TO RELATED APPLICATIONS

This is a national stage application under 35 U.S.C. § 371 of International Application No. PCT/US2010/041092, filed Jul. 6, 2010, which in turn claims priority under 35 U.S.C. § 119(e) to U.S. Provisional Application Ser. No. 61/328,168, filed Apr. 26, 2010; 61/266,985, filed Dec. 4, 2009 and 61/223,692, filed Jul. 7, 2009, the contents of each of which is incorporated by reference into the present disclosure.

STATEMENT AS TO FEDERALLY SPONSORED RESEARCH OR DEVELOPMENT

This invention was made with government support under the Contract No. RO1 EY011386, EY017293 and EY016985 awarded by the National Institutes of Health. The government has certain rights to the invention.

FIELD OF THE INVENTION

This invention relates to compositions and methods for the diagnosis of autoimmune diseases and for their treatments.

BACKGROUND

Autoimmune diseases arise from an overactive immune response of the body against substances and tissues normally present in the body in which the body actually attacks its own cells. The immune system mistakes some part of the body as a pathogen and attacks it. This may be restricted to certain organs (e.g. in thyroiditis) or involve a particular tissue in different places (e.g. Goodpasture's disease which may affect the basement membrane in both the lung and the kidney). The treatment of autoimmune diseases is typically with immunosuppression—medication which decreases the immune response. The mechanisms of autoimmune diseases are not well understood and the treatment options are limited.

Examples of autoimmune diseases include Coeliac disease, diabetes mellitus type 1 (IDDM), systemic lupus erythematosus (SLE), Sjögren's syndrome, Churg-Strauss Syndrome, Hashimoto's thyroiditis, Graves' disease, idiopathic thrombocytopenic purpura, and rheumatoid arthritis (RA).

Sjögren's syndrome (SjS) is a chronic autoimmune inflammatory disease characterized by lymphocytic infiltration and destruction of lacrimal glands (LG) and salivary gland function (SG). SjS can occur independently (primary SjS) or in conjunction with another autoimmune disease (secondary SjS); both forms may progress to systemic disease of other organs. In both primary and secondary SjS, the presenting symptoms of ocular surface dryness, corneal irritation and increased susceptibility to infection overlap with symptoms of simple keratoconjunctivitis sicca (KCS). Despite the potentially unique disease profile that is likely to be manifested in the tears of primary and secondary SjS patients, no tear biomarkers have been established as diagnostic for either form.

Definition of tear biomarkers which can predict disease severity would be valuable diagnostically in combination with existing clinical strategies, potentially contributing to different choices of therapy and improved disease outcome for SjS as well as for other autoimmune diseases. Since sensitivity of detection and stability of biomarkers and detection reagents are significant challenges given the limited sample sizes and extensive protease content of even normal tears, development of alternative detection strategies for tear biomarkers is clearly warranted. This invention satisfied this need and provides related advantages as well.

SUMMARY OF THE INVENTION

One aspect of the invention provides a method for determining whether a mammal is likely to develop autoimmune disease, comprising, or alternatively consisting essentially of or yet further consisting of measuring an expression level or activity level of at least one first polypeptide selected from the group Ctss, Ctsh, Ctsr, Ctsw, Ctsz, Ifng, Il6ra, Il10, Il10ra, Il15, Tnfa, or Lcn-2, and/or at least one second polypeptide selected from the group lactoperoxidase, lactoferrin or lysozyme in a sample of tears isolated from the mammal, wherein an increased expression level or increased activity level of the first polypeptide or a decreased expression level or decreased activity level of the second polypeptide, as compared to a suitable control, indicates that the mammal is likely to develop autoimmune disease. In a further aspect, measuring the expression level or activity level of Apo-F is excluded from the method.

Also provided is a method for aiding in the diagnoses of autoimmune disease in a mammal, comprising, or alternatively consisting essentially of or yet further consisting of measuring an expression level or activity level of at least one first polypeptide selected from the group Ctss, Ctsh, Ctsr, Ctsw, Ctsz, Ifng, Il6ra, Il10, Il10ra, Il15, Tnfa, Apo-F, or Lcn-2, and/or at least one second polypeptide selected from the group lactoperoxidase, lactoferrin or lysozyme in a sample of tear isolated from the mammal, wherein an increased expression level or increased activity level of the first polypeptide or a decreased expression level or decreased activity level of the second polypeptide, as compared to a suitable control, indicates a likely positive diagnosis of autoimmune disease for the mammal, thereby aiding in the diagnosis. In a further aspect, measuring the expression level or activity level of Apo-F is excluded from the method.

Further provided is a method for diagnosing relative severity of autoimmune disease in a mammal, comprising, or alternatively consisting essentially of or yet further consisting of measuring an expression level or activity level of at least one first polypeptide selected from the group Ctss, Ctsh, Ctsr, Ctsw, Ctsz, Ifng, Il6ra, Il10, Il10ra, Il15, Tnfa, Apo-F, or Lcn-2, or at least one second polypeptide selected from the group lactoperoxidase, lactoferrin or lysozyme in a sample of tear from the mammal, wherein a relatively higher expression level or activity level of the first polypeptide or a relatively lower expression level or activity level of the second polypeptide, as compared to a suitable control, indicates that the individual has relatively more severe autoimmune disease. In a further aspect, measuring the expression level or activity level of Apo-F is excluded from the method.

In some embodiments of the methods of the invention, the first polypeptide is one or more of Ctss, Apo-F or Lcn-2. In a further aspect, measuring the expression level or activity level of Apo-F is excluded from the method.

Another aspect of the invention provides a method of treating a mammal suffering from or at risk of developing autoimmune disease and identified as being in need of such treatment by any one of the methods provided above, comprising, or alternatively consisting essentially of or yet further consisting of administering an effective amount of a suitable therapy to the mammal, thereby treating the mammal. Non-limiting examples of suitable therapies include administration of an effective amount of cyclosporin, cevimeline, pilocarpine, a nonsteroidal anti-inflammatory drug, a corticosteroid, an immunosuppressive drug or a disease-modifying antirheumatic drug. In one aspect, the mammal is a human patient.

In another aspect, the invention provides a method for treating a mammal suffering from or at risk of developing autoimmune disease, comprising, or alternatively consisting essentially of or yet further consisting of administering to the mammal an effective amount of an agent inhibiting the expression or activity of one or more of a polypeptide selected from Ctss, Ctsh, Ctsr, Ctsw or Ctsz. In one aspect, the polypeptide is Ctss. In one embodiment, the mammal is a human patient.

Autoimmune diseases that can be diagnosed or treated by the methods of the invention include, without limitation, Coeliac disease, diabetes mellitus type 1 (IDDM), lupus erythematosus, systemic lupus erythematosus (SLE), Sjögren's syndrome, Churg-Strauss Syndrome, Hashimoto's thyroiditis, Graves' disease, idiopathic thrombocytopenic purpura, rheumatoid arthritis (RA), ankylosing spondylitis, Crohns disease, dermatomyositis, Goodpasture's syndrome, Guillain-Barré syndrome (GBS), mixed Connective tissue disease, multiple sclerosis, myasthenia gravis, narcolepsy, pemphigus vulgaris, pernicious anaemia, psoriasis, psoriatic arthritis, polymyositis, primary biliary cirrhosis, relapsing polychondritis, temporal arteritis, ulcerative colitis, vasculitis and Wegener's granulomatosis.

BRIEF DESCRIPTION OF THE DRAWINGS

FIG. 10 shows human tear proteins separated by SDS-PAGE after being eluted into cathepsin S assay buffer from Schirmer's test strips and being processed to analyze cathepsin S.

DETAILED DESCRIPTION OF THE INVENTION

Figure 1:
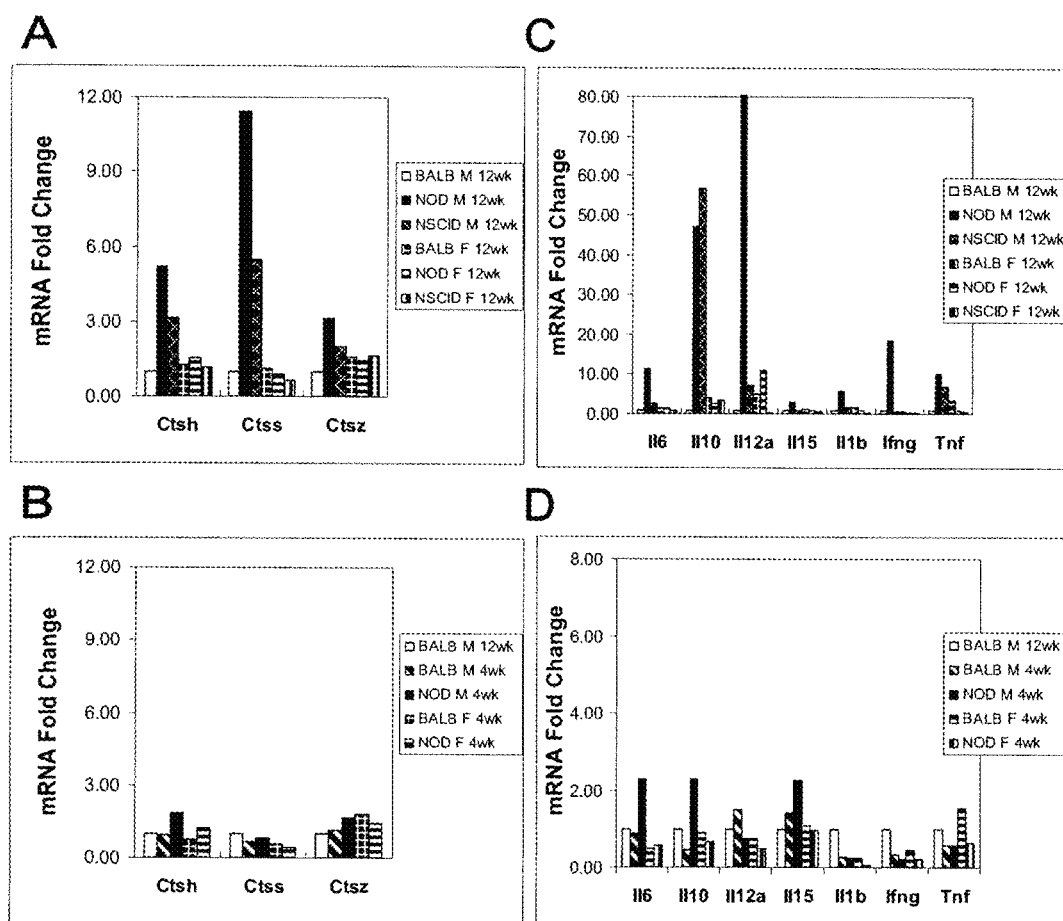
FIGS. 1A through 1D depict validation of microarray data and expanded investigation for genes of interest by real-time RT-PCR in LG from NOD, NOD SCID and BALB/c mice. Differentially expressed genes in LGs of NOD and BALB/c mice, suggested by microarray analysis, encoding Ctsh, Ctss, Ctsz and macrophage-produced cytokines were validated by real-time RT-PCR in LGs from 12-week-old NOD mice, matched BALB/c control, and more animal groups as shown in the figure panels. Certain relevant cytokines that were not detected by microarray due to its relative insensitivity were also re-evaluated in this study. Triplicates of each reaction were set up in parallel. The results were repeated 2-3 times and reproduced with RNAs from different batches of animals. The comparisons between different samples were conducted using the formulation of $\Delta\Delta Ct$ study built into the ABI SDS 2.1 software. The expression level of all the genes in 12-week-old male BALB/c mice were designated as 1.0, and the expression levels of these genes in the rest of mice were compared to that in 12-week-old male BALB/c mice.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, 3$^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5$^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

The term "antigen" is well understood in the art and includes substances which are immunogenic. The Ctss is an example of an antigen.

A "native" or "natural" or "wild-type" antigen is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

In one aspect, the "biological activity" means the ability of the antibody to selectively bind its epitope protein or fragment thereof as measured by ELISA or other suitable methods. Biologically equivalent antibodies, include but are not limited to those antibodies, peptides, antibody fragments, antibody variant, antibody derivative and antibody mimetics that bind to the same epitope as the reference antibody.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')$^2$ fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A hybridoma is a cell that is produced in the laboratory from the fusion of an antibody-producing lymphocyte and a non-antibody producing cancer cell, usually a myeloma or lymphoma. A hydridoma proliferates and produces a continuous supply of a specific monoclonal antibody.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by heavy chain constant region genes.

The terms "protein", "polypeptide" and "peptide" are used interchangeably herein when referring to a gene product.

An "autoimmune disease" intends a disease that arises from an overactive immune response of the body against substances and tissues normally present in the body in which the body actually attacks its own cells. Examples of autoimmune diseases include, without limitation, Coeliac disease, diabetes mellitus type 1 (IDDM), lupus erythematosus, systemic lupus erythematosus (SLE), Sjögren's syndrome, Churg-Strauss Syndrome, Hashimoto's thyroiditis, Graves' disease, idiopathic thrombocytopenic purpura, rheumatoid arthritis (RA), ankylosing spondylitis, Crohns disease, dermatomyositis, Goodpasture's syndrome, Guillain-Barré syndrome (GBS), mixed Connective tissue disease, multiple sclerosis, myasthenia gravis, narcolepsy, pemphigus vulgaris, pernicious anaemia, psoriasis, psoriatic arthritis, polymyositis, primary biliary cirrhosis, relapsing polychondritis, temporal arteritis, ulcerative colitis, vasculitis and Wegener's granulomatosis.

"Ctss" or "cathepsin S" is member of the peptidase C1 family, a lysosomal cysteine proteinase that may participate in the degradation of antigenic proteins to peptides for presentation on MHC class II molecules. The encoded protein can function as an elastase over a broad pH range in alveolar macrophages. Representative sequences include UniProtKB: P25774 and Entrez Gene: 1520.

"Ctsh" or "cathepsin H" is a lysosomal cysteine proteinase important in the overall degradation of lysosomal proteins. It is composed of a dimer of disulfide-linked heavy and light chains, both produced from a single protein precursor. The encoded protein, which belongs to the peptidase C1 protein family, can act both as an aminopeptidase and as an endopeptidase. Increased expression of this gene has been correlated with malignant progression of prostate tumors. Representative sequences include UniProtKB: P09668 and Entrez Gene: 1512.

"Ctsr" or "cathepsin R" is a lysosomal cysteine proteinase and member of the peptidase C1 family. Ctsr was identified as a candidate lung tumor susceptibility gene identified through whole-genome association analyses in inbred mice. Representative sequences include UniProKB: ☐9JLA9 and GeneBank Protein ID: NP_064680.

"Ctsw" or "cathepsin W", a member of the peptidase C1 family, is a cysteine proteinase that may have a specific function in the mechanism or regulation of T-cell cytolytic activity. The encoded protein is found associated with the membrane inside the endoplasmic reticulum of natural killer and cytotoxic T-cells. Expression of this gene is up-regulated by interleukin-2 Representative sequences include UniProtKB: P56202 and Entrez Gene: 1521.

"Ctsz" or "cathepsin Z" is a lysosomal cysteine proteinase and member of the peptidase C1 family. It exhibits both carboxy-monopeptidase and carboxy-dipeptidase activities. The encoded protein has also been known as cathepsin X and cathepsin P. This gene is expressed ubiquitously in cancer cell lines and primary tumors and, like other members of this family, may be involved in tumorigenesis. Representative sequences include UniProtKB: Q9UBR2 and Entrez Gene: 1522.

"Ifng" or "interferon, gamma" is a cytokine critical for innate and adaptive immunity against viral and intracellular bacterial infections and for tumor control. Aberrant IFNG expression is associated with a number of autoinflammatory and autoimmune diseases. The importance of IFNG in the immune system stems in part from its ability to inhibit viral replication directly, but most importantly derives from its immunostimulatory and immunomodulatory effects. IFNG is produced predominantly by natural killer (NK) and natural killer T (NKT) cells as part of the innate immune response, and by CD4 and CD8 cytotoxic T lymphocyte (CTL) effector T cells once antigen-specific immunity develops. Representative sequences include UniProtKB: P01579 and Entrez Gene: 3458.

Il6ra" or "interleukin 6 receptor alpha subunit" is a potent pleiotropic cytokine that regulates cell growth and differentiation and plays an important role in immune response. The protein encoded by this gene is a subunit of the receptor complex for IL6. The IL6 receptor is a protein complex consisting of this protein and interleukin 6 signal transducer (IL6ST/GP130/IL6-beta), a receptor subunit also shared by many other cytokines Dysregulated production of IL6 and this receptor are implicated in the pathogenesis of many diseases, such as multiple myeloma, autoimmune diseases and prostate cancer. Alternatively spliced transcript variants encoding distinct isoforms have been reported. Representative sequences include UniProtKB: P08887 and Entrez Gene: 3570.

"Il10" or "interleukin 10" is a cytokine produced primarily by monocytes and to a lesser extent by lymphocytes. This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production. This cytokine can block NF-kappa B activity, and is involved in the regulation of the JAK-STAT signaling pathway. Knockout studies in mice suggested the function of this cytokine as an essential immunoregulator in the intestinal tract. Representative sequences include UniProtKB: P22301 and Entrez Gene: 3586.

"Il10ra" or "interleukin 10 receptor, alpha" is a receptor for interleukin 10. This protein is structurally related to interferon receptors. It has been shown to mediate the immunosuppressive signal of interleukin 10, and thus inhibits the synthesis of proinflammatory cytokines. This receptor is reported to promote survival of progenitor myeloid cells through the insulin receptor substrate-2/PI 3-kinase/AKT pathway. Activation of this receptor leads to tyrosine phosphorylation of JAK1 and TYK2 kinases. Representative sequences include UniProtKB: Q13651 and Entrez Gene: 3587.

Il15" or "interleukin 15" is a cytokine that regulates T and natural killer cell activation and proliferation. This cytokine and interleukin 2 share many biological activities. They are found to bind common hematopoietin receptor subunits, and may compete for the same receptor, and thus negatively regulate each other's activity. The number of CD8+ memory cells is shown to be controlled by a balance between this cytokine and IL2. This cytokine induces the activation of JAK kinases, as well as the phosphorylation and activation of transcription activators STAT3, STAT5, and STAT6. Studies of the mouse counterpart suggested that this cytokine may increase the expression of apoptosis inhibitor BCL2L1/BCL-x(L), possibly through the transcription activation activity of STAT6, and thus prevent apoptosis. Two alternatively spliced transcript variants of this gene encoding the same protein have been reported. Representative sequences include UniProtKB: P40933 and Entrez Gene: 3600.

"TNFα or Tnfa" or "tumor necrosis factor alpha" is a multifunctional proinflammatory cytokine that belongs to the tumor necrosis factor (TNF) superfamily. This cytokine is mainly secreted by macrophages. It can bind to, and thus functions through its receptors TNFRSF1A/TNFR1 and TNFRSF1B/TNFBR. This cytokine is involved in the regulation of a wide spectrum of biological processes including cell proliferation, differentiation, apoptosis, lipid metabolism, and coagulation. This cytokine has been implicated in a variety of diseases, including autoimmune diseases, insulin resistance, and cancer. Knockout studies in mice also suggested the neuroprotective function of this cytokine Representative sequences include UniProtKB: P01375 and Entrez Gene: 7124.

"Apo-F" or "apolipoprotein F" is one of the minor apolipoproteins found in plasma. This protein forms complexes with lipoproteins and may be involved in transport and/or esterification of cholesterol. Representative sequences include UniProtKB: Q13790 and Entrez Gene: 319.

"Lcn-2", "lipocalin 2", or "neutrophil gelatinase-associated lipocalin", is expressed in both mice and humans, and has been shown to be highly expressed in pancreatic islets, bone marrow, and SG. Until now its expression in LG has not been investigated but microarray data suggest moderate to high levels of expression. It is implicated in diverse bioprocesses including iron-siderophore binding in bacterial infections as a component of the innate immune system, modulation of inflammation, and is a marker closely related to obesity and insulin resistance (Flo, et al. (2004) Nature 432(7019):917-21, 13). Lcn-2 transports small lipophilic substances. Representative sequences include UniProtKB: P80188 and Entrez Gene: 3934.

"Lactoperoxidase", "Salivary peroxidase" or "LPO" has representative sequences including UniProtKB: P22079 and Entrez Gene: 4025.

"Lactoferrin" or "LTF" is a member of the transferrin family of genes and its protein product is found in the secondary granules of neutrophils. The protein is a major iron-binding protein in milk and body secretions with an antimicrobial activity, making it an important component of the non-specific immune system. The protein demonstrates a broad spectrum of properties, including regulation of iron homeostasis, host defense against a broad range of microbial infections, anti-inflammatory activity, regulation of cellular growth and differentiation and protection against cancer development and metastasis. Representative sequences include UniProtKB: P02788 and Entrez Gene: 4057.

"Lysozyme" or "LYZ" has a natural substrate that is the bacterial cell wall peptidoglycan (cleaving the beta[1-4] glycosidic linkages between N-acetylmuramic acid and N-acetylglucosamine). Lysozyme is one of the anti-microbial agents found in human milk, and is also present in spleen, lung, kidney, white blood cells, plasma, saliva, and tears. Missense mutations in LYZ have been identified in heritable renal amyloidosis. Representative sequences include UniProtKB: P61626 and Entrez Gene: 4069.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A "mammal" is a class of vertebrate animals whose females are characterized by the possession of mammary glands while both males and females are characterized by sweat glands, hair, three middle ear bones used in hearing, and a neocortex region in the brain. Non-limiting examples of a mammal include a simian, a murine, a bovine, an equine, a porcine or an ovine. In one aspect, a mammal is a mouse. In another aspect, a mammal is a rat. In yet another aspect, a mammal is a rabbit. In yet another aspect, a mammal is a human.

"Expression" as applied to a gene or a protein, refers to the production of the mRNA transcribed from the gene or the protein product encoded by the gene. In one aspect, "expression" level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest.

"Overexpression" or "underexpression" refers to increased or decreased expression, or alternatively a differential expression, of a gene in a test sample as compared to the expression level of that gene in the control sample. In one aspect, the test sample is a diseased cell, and the control sample is a normal cell. In another aspect, the test sample is an experimentally manipulated or biologically altered cell, and the control sample is the cell prior to the experimental manipulation or biological alteration. In yet another aspect, the test sample is a sample from a patient, and the control sample is a similar sample from a healthy individual. In a yet further aspect, the test sample is a sample from a patient and the control sample is a similar sample from patient not having the desired clinical outcome. In one aspect, the differential expression is about 1.5 times, or alternatively, about 2.0 times, or alternatively, about 2.0 times, or alternatively, about 3.0 times, or alternatively, about 5 times, or alternatively, about 10 times, or alternatively about 50 times, or yet further alternatively more than about 100 times higher or lower than the expression level detected in the control sample. Alternatively, the gene is referred to as "over expressed" or "under expressed". Alternatively, the gene may also be referred to as "up regulated" or "down regulated".

An "internal control" or "house keeping" gene refers to any constitutively or globally expressed gene whose presence enables an assessment of the gene of interests expression level. Such an assessment comprises a determination of the overall constitutive level of gene transcription and a control for variation in sampling error. Examples of such genes include, but are not limited to, β-actin, the transferrin receptor gene, GAPDH gene or equivalents thereof. In some aspects of this invention, the internal control or house keeping gene is the suitable control.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The phrase "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

When gene or protein expression level "is used as a basis" for selecting a patient for a treatment described herein, the gene or protein expression level is measured before and/or during treatment, and the values obtained are used by a clinician in assessing any of the following: (a) probable or likely suitability of an individual to initially receive treatment(s); (b) responsiveness to treatment; (c) probable or likely suitability of an individual to continue to receive treatment(s); (d) adjusting dosage; (e) predicting likelihood of clinical benefits. As would be well understood by one in the art, measurement of the gene expression level in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease.

"An effective amount" intends to indicate the amount of a compound or agent administered or delivered to the patient which is most likely to result in the desired treatment outcome. The amount is empirically determined by the patient's clinical parameters including, but not limited to the stage of disease, age, gender, histology, and likelihood for recurrence.

"Sjögren's syndrome" or "SjS" affects an estimated 4 million Americans, with 9 out of 10 patients being women (Lemp (2005) Am J Ophthalmol. 140(5):898-9; Hansen., et al. (2005) Curr Opin Rheumatol. 17(5):558-65). SjS is the second most common autoimmune disease in the United States; research into the improved diagnosis and treatment for these autoimmune disorders has long been recognized by the Office for Research on Women's Health (ORWH) as a priority. The lacrimal gland (LG) is responsible for secretion of proteins and fluid to sustain the health of the ocular surface (OS). SjS is characterized by lymphocytic infiltration of LG and salivary gland (SG), followed by development of functional quiescence (e.g., inability to secrete fluid and proteins) as well as the eventual inflammatory destruction of these glands. The ocular surface of SjS patients becomes desiccated and prone to infection because of the functional quiescence of the gland as well as changes in the spectrum of secreted proteins, leading to severe corneal damage and in some cases, blindness. SjS can occur independently (primary Sj S) or in conjunction with another autoimmune disease such as rheumatoid arthritis or systemic lupus erythematosus (secondary SjS). Primary SjS in particular is associated with significant effects on other organs including the brain, kidneys, lungs, pancreas and gastrointestinal tract (Hansen., et al. (2005) Curr Opin Rheumatol. 17(5):558-65)). A diagnosis of primary SjS is also associated with a significantly increased risk of B cell lymphoma. In primary and secondary SjS, the presenting symptoms overlap with other keratoconjunctivitis sicca (KCS) disorders while for secondary SjS, the presenting symptoms also overlap with many other autoimmune diseases. The SjS Foundation estimates that it requires nearly 7 years for the typical patient to receive a diagnosis of SjS, because the symptoms overlap so substantially with those for other diseases. Since the tears and saliva are thought to be uniquely altered in SjS, it is astounding that there are currently no tear or salivary biomarkers that are recognized as diagnostic for SjS, in particular for primary SjS, and which can aid in the early identification of this subset of SjS patients that will experience more severe disease. Achievement of the goals proposed in this application, detection and validation of unique tear biomarkers that are released into tears in proportion to the severity of the disease and development of new paradigms for assay of such materials in tear fluid, would be critical first steps in the ultimate goal of identification and earlier treatment of SjS patients to arrest aggressive disease development. Since SjS, like most autoimmune diseases, is so strongly manifested in post-menopausal women relative to other populations, the success of this invention will also constitute a critical advance in diagnosis of a disease that has a tremendous impact on women's health.

Disease models for SjS include the NOD mouse, a genetic model and the IL-1-injected BALB/c mouse. They represent two models of inflammatory autoimmune LG disease. These two models differ in that one is a genetic model and the other is an experimentally-induced disease model which uses cytokine injection to induce LG disease.

"NOD mouse" is a well-studied genetic animal model for human insulin-dependent diabetes mellitus and SjS (Barabino, et al. (2004) Invest Ophthalmol V is Sci. 45(6):1641-6). This strain spontaneously develops lymphocytic infiltration in submandibular glands (sialoadenitis) and LG (dacryoadenitis), and diabetes. Male NOD mice are significantly more susceptible to dacryoadenitis, and disease development in the female mouse LG is minimal. This differs from the human disease since SjS is more prevalent in women. Despite this difference, the lymphocytic infiltration into the LG of male mice is profound and occurs as early as 6 weeks, along with decreased production of tear fluid. The male NOD mouse LG also exhibits significant lipid deposition, a feature of human SjS. This genetic model system has been useful in generating strong leads for the protein biomarkers in tear fluid that are proposed to increase in disease: CtsS, Apo-F and Lcn-2. Male NOD mice, which develop the severe autoimmune inflammatory LG disease, will be utilized for tear fluid collection, in parallel with measurement of tear flow and corneal, conjunctival and LG integrity and inflammation. The ages of mice examined can span disease onset (4-12 weeks), intermediate development of disease (12 weeks-6 months) and advanced disease (6-12 months). Age- and gender-matched BALB/c mice can be used as controls.

"IL-1-injected BALB/c mouse" is a mouse model of induced inflammatory autoimmune disease that will be utilized as a second model is based on a single injection of IL-1β or IL-1α into LG of female BALB/c or C57BL/6 mice, which induces a reversible inflammatory aqueous tear deficiency (Zoukhri, et al. (2002) Invest Ophthalmol V is Sci. 43(5):1429-36), followed by recovery within a defined timetable which is dependent upon the injected strain.

Schirmer's test strips have traditionally been used for auantitative measurement of tear production. The standardized Schirmer test strip consists of a 5×35 mm strip of Whatman #41 filter paper; the paper has a notch located 5 mm from one end of the strip. The strips are commercially available from vendors such as Alcon Manufacturing, Ltd. The notched end of the strip can be is rounded. As described in U.S. Pat. No. 5,006,310 a Schirmer Tear Test is performed by bending the strip at the notch (~120° bend). The rounded end of the Schirmer Tear Test strip is then inserted into the lower conjunctival sac of each eye. The eyes are then closed and the strip is progressively wetted by capillary action drawing up tears as they are produced. The distance the tear migration front has moved is measured after 5 minutes. The migration distance of the tears is measured from the notch of the strip as the zero point. Reading the test involves removing the strip from the eye and placing it against a scale graduated in millimeters. 15 mm of wetting in 5 minutes is considered normal. For tear production levels, it has been recommended that the tear migration front be measured as close to the 5 minute time mark as possible because the tear front will continue to migrate up the strip after the strip is removed from the eye. Thus, late readings give rise to results that are artificially high.

As used herein, the term "detectable label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorometric labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

Descriptive Embodiments

It has been discovered herein that the expression level of activity certain peptides are altered in tears in patients having an autoimmune disease. The altered expression level or activity of these polypeptides then can be used as biomarker for diagnosis or prediction of autoimmune diseases, methods of restoring the expression level or activity, therefore, can be used to treat the autoimmune disease.

Thus, the invention, in one aspect, provides diagnostic methods, which are based, at least in part, on determination of the expression or activity levels of a polypeptide selected from the group Ctss, Ctsh, Ctsr, Ctsw, Ctsz, Ifng, Il6ra, Il10, Il10ra, Il15, Tnfa, Apo-F, Lcn-2, lactoperoxidase, lactoferrin or lysozyme. In one aspect at least one polypeptide expression level is determined, in another at least two, or alternatively at least three, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12, or alternatively at least 13, or alternatively at least 14, or alternatively at least 15, or alternatively all 16 expression levels are determined. In a further aspect, measuring the expression level or activity level of Apo-F is excluded from the method.

In one aspect, the expression or activity levels of a polypeptide selected from the group Ctss, Ctsh, Ctsr, Ctsw, Ctsz, Ifng, Il6ra, Il10, Il10ra, Il15, Tnfa, Apo-F, Lcn-2, lactoperoxidase, lactoferrin or lysozyme is used as a basis for selecting a patient for a treatment. In one aspect at least one polypeptide expression level is determined, in another at least two, or alternatively at least three, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12, or alternatively at least 13, or alternatively at least 14, or alternatively at least 15, or alternatively all 16 expression levels are determined. In a further aspect, measuring the expression level or activity level of Apo-F is excluded from the method.

In one embodiment, the invention provides a method for determining whether a mammal is likely to develop Sjögren's syndrome, comprising, or alternatively consisting essentially of or yet further consisting of measuring an expression level or activity level of at least one first polypeptide selected from the group Ctss, Ctsh, Ctsr, Ctsw, Ctsz, Ifng, Il6ra, Il10, Il10ra, Il15, Tnfa, Apo-F, or Lcn-2, and/or at least one second polypeptide selected from the group lactoperoxidase, lactoferrin or lysozyme in a sample of tear isolated from the mammal, wherein an increased expression level or increased activity level of the first polypeptide or a decreased expression level or decreased activity level of the second polypeptide, as compared to a suitable control, indicates that the mammal is likely to develop autoimmune disease. In one aspect at least one polypeptide expression level of a first polypeptide is determined, in another at least two, or alternatively at least three, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12, or alternatively all 13 expression levels are determined. In one aspect at least one polypeptide expression level of a second polypeptide is determined, in another at least two, or alternatively all three of the second polypeptides expression levels are determined. In a further aspect, measuring the expression level or activity level of Apo-F is excluded from the method.

Methods of measuring the expression level of polypeptide are known in the art. Non-limiting examples include Western blot, gel electrophoresis, ELISA, fluorometric analysis mass spectrometry, or protein array.

"Activity level" as applied to a protein, refers to the enzymatic activity level of the protein. Determination of the activity level can be made based on the capability of the protein to catalyze a chemical or biological reaction using one or more substrates. In one aspect, activity level is protease activity level which can be determined by the protein's capability to hydrolyze a peptide sequence at a specific location.

Methods of measuring the activity level of a polypeptide are known in the art. For example, for polypeptides that have protease activities, their activities can be measured by their capability to hydrolyze a substrate peptide. Protease activity measuring kits for various proteases including Ctss are commercially available from vendors such as Sigma-Aldrich (St. Louis, Mo.) and BioVision Inc. (Mountain View, Calif.).

Measurement of protein expression level or activity level can be made in comparison to suitable controls. Suitable internal controls can be a protein or other agent that is constantly present in the same sample from different mammals. Suitable internal controls can also be the total volume of samples collected, such as the total volume of tear fluid. Suitable external controls can also used for determination of the protein expression level or activity level. Suitable external controls can be a mammal that does not appear to have the disease of interest. Suitable external controls can also be historical samples collected that have been proven to be from mammals that do not have the disease. In one aspect, a suitable external control for a NOD mouse is a BALB/c mouse.

Collection of samples of tear can be done with methods known in the art and described briefly herein. Stimulation can be applied when needed, for example by eye-wash prior to sample collection. For the purpose of illustration only, tears can be collected onto a Schirmer's test strip containing or embedded with a quantitatively-labeled substrate, e.g., an antibody coupled to a detectable marker such as a fluorometric label or substrate. The polypeptide or protein in the tear will react with the detectably labeled substrate allowing measurement of the expression level or activity level of the one first and/or second polypeptide.

As used herein, a mammal that is "likely to develop autoimmune disease" is a mammal that is more likely than not to develop autoimmune disease.

In another embodiment, the invention provides a method for aiding in diagnosing autoimmune disease in a mammal, comprising, or alternatively consisting essentially of or yet further consisting of measuring an expression level or activity level of at least one first polypeptide selected from the group Ctss, Ctsh, Ctsr, Ctsw, Ctsz, Ifng, Il6ra, Il10, Il10ra, Il15, Tnfa, Apo-F, or Lcn-2, and/or at least one second polypeptide selected from the group lactoperoxidase, lactoferrin or lysozyme in a sample of tear isolated from the mammal, wherein an increased expression level or increased activity level of the first polypeptide or a decreased expression level or decreased activity level of the second polypeptide, as compared to a suitable control, indicates a likely positive diagnosis of autoimmune disease for the mammal, thereby aiding in the diagnosis. In one aspect at least one polypeptide expression level of a first polypeptide is determined, in another at least two, or alternatively at least three, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12, or alternatively all 13 expression levels are determined. In one aspect at least one polypeptide expression level of a second polypeptide is determined, in another at least two, or alternatively all three of the second polypeptides expression levels are determined. In a further aspect, measuring the expression level or activity level of Apo-F is excluded from the method.

In one aspect, aiding in the diagnosis refers to providing confirmation to existing diagnosis. In another aspect, aiding in the diagnosis refers to using the diagnosis method in a panel of diagnosis methods, each method of the panel contributing to a final diagnosis. In yet another aspect, aiding in the diagnosis refers to that more than one of the markers recited herein are used in combination to make a diagnosis.

In another embodiment, the invention provides a method for diagnosing relative severity of autoimmune disease in a mammal, comprising, or alternatively consisting essentially of or yet further consisting of measuring an expression level or activity level of a first polypeptide selected from the group Ctss, Ctsh, Ctsr, Ctsw, Ctsz, Ifng, Il6ra, Il10, Il10ra, Il15, Tnfa, Apo-F, or Lcn-2, or a second polypeptide selected from the group lactoperoxidase, lactoferrin or lysozyme in a sample of tear from the mammal, wherein a relatively higher expression level or activity level of the first polypeptide or a relatively lower expression level or activity level of the second polypeptide, as compared to a suitable control, indicates that the individual has relatively more severe autoimmune disease. In one aspect at least one polypeptide expression level of a first polypeptide is determined, in another at least two, or alternatively at least three, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12, or alternatively all 13 expression levels are determined. In one aspect at least one polypeptide expression level of a second polypeptide is determined, in another at least two, or alternatively all three of the second polypeptides expression levels are determined. In a further aspect, measuring the expression level or activity level of Apo-F is excluded from the method.

It is to be intended, although not always explicitly stated, that the methods of this invention can be further modified by measuring or determining the expression level or activity level of at least two, or alternatively at least three, or alternatively at least four, or alternatively at least five, or alternatively at least six, or alternatively at least seven, or alternatively at least eight of the polypeptides are measured and compared to suitable controls, and a diagnosis can be made based on their overall expression level or activity level changes.

In one aspect of the above embodiments, the first polypeptide is selected from the group Ctss, Apo-F or Lcn-2. In a further aspect, measuring the expression level or activity level of Apo-F is excluded from the method.

Further, it has now been discovered that, similar to a mouse, human patients in which Apo-F is dispersedly distributed within cytoplasmic and secretory vesicle-like organelles may likely be suffering from autoimmune disease or at risk of developing autoimmune disease, whereas human individuals in which Apo-F is located at the cytoplasmic face of the plasma membrane in the acinar cells are likely not suffering from autoimmune disease or at risk of developing autoimmune disease. The dispersed distribution of ApoF in NOD mouse LG and certain human LG is believed to result from missorting of ApoF in the acinar cells.

Without being bound by theory, Applicants' finding indicates that the disparate distribution patterns of missorted proteins, such as Apo-F as well as CATS, as observed in the NOD mouse model compared to healthy mice, are markers for the diagnosis of autoimmune disease, not only in mouse, but also in human and other mammals. Accordingly, the presence of Apo-F or CATS at the cytoplasmic face of the plasma membrane in acinar cells in a LG from a mammal indicates that the mammal is not likely suffering from autoimmune disease or is not at risk of developing autoimmune disease. A dispersed distribution of Apo-F or CATS within cytoplasmic or secretory vesicle-like organelles in acinar cells in a LG from a mammal indicates that the mammal is suffering from autoimmune disease or is at risk of developing autoimmune disease.

Accordingly, one aspect of the invention provides a method for determining whether a mammal is likely to develop autoimmune disease, comprising determining the presence of a protein selected from CATS or APO-F or any missorted protein as observed in the NOD mouse LG, in an acinar cell isolated from the lacrimal gland or salivary gland of the mammal, wherein the mammal is likely to develop autoimmune disease if more than about 10%, or alternatively about 20%, about 30%, about 40%, about 50%, about 60%, about 70%, about 80%, about 90%, or about 95% of the protein in the cell is present not in proximity to the basolateral membrane of the cell. As is apparent to those skilled in the art, a failure of this finding indicates that the mammal is not likely to develop autoimmune disease.

Further provided is a method for aiding in diagnosing autoimmune disease in a mammal, comprising determining the presence of a protein selected from CATS or APO-F or any missorted protein as observed in the NOD mouse LG, in an acinar cell isolated from the lacrimal gland or salivary gland of the mammal, wherein presence of more than about 10%, or alternatively about 20%, about 30%, about 40%, about 50%, about 60%, about 70%, about 80%, about 90%, or about 95% of the protein in the cell not in proximity to the basolateral membrane of the cell indicates a likely positive diagnosis of autoimmune disease for the mammal, thereby aiding in the diagnosis. As is apparent to those skilled in the art, a failure of this finding indicates that the mammal is not a positive diagnosis to develop autoimmune disease.

As used in herein, the term "proximity" intends a distance in a cell that is relative small compared to the diameter of the cell. In one aspect, not in proximity to the basolateral membrane of the cell means having a distance from the basolateral membrane of the cell that is at least about $\frac{1}{20}$, or alternatively about $\frac{1}{10}$, about $\frac{1}{9}$, about $\frac{1}{8}$, about $\frac{1}{7}$, about $\frac{1}{6}$, about $\frac{1}{5}$, about $\frac{1}{4}$, or about $\frac{1}{3}$ of the diameter of the cell.

In another aspect of the above embodiments, the method further comprises diagnosing the mammal with a test selected from the group of Schirmer test, a slit-lamp examination, a radiological test, or a blood test. The results from this additional test can be combined with the methods provided in the above embodiment to assist diagnosis. In this aspect, the methods as disclosed herein aid in the diagnosis of autoimmune disease when combined with other known or yet to be developed diagnostic methods.

Schirmer's test determines whether the eye produces enough tears to keep it moist. This test is used when a person experiences very dry eyes or excessive watering of the eyes. Schirmer's test uses paper strips inserted into the eye for several minutes to measure the production of tears. This technique measures basic tear function. Applicants have adapted these filter paper strips in common usage to collect human tears for measurement of protein activities.

A slit-lamp examination uses an instrument, slit-lamp, to provide a magnified, three-dimensional view of the different parts of the eye. The slit lamp is an instrument consisting of a high-intensity light source that can be focused to shine a thin sheet of light into the eye. It is used in conjunction with a biomicroscope. The lamp facilitates an examination of the anterior segment, or frontal structures and posterior segment, of the human eye, which includes the eyelid, sclera, conjunctiva, iris, natural crystalline lens, and cornea. The binocular slit-lamp examination provides stereoscopic magnified view of the eye structures in detail, enabling anatomical diagnoses to be made for a variety of eye conditions.

A radiological procedure can also be used as a reliable and accurate way of diagnosing autoimmune disease. A contrast agent is injected into the parotid duct (of Stensen), which is a duct opening from the cheek into the vestibule of the mouth opposite the neck of the upper second molar tooth. Widespread puddling of the injected contrast scattered throughout the gland indicates autoimmune disease.

Blood tests can be done to determine if a patient has high levels of antibodies that are indicative of the condition, such as anti-nuclear antibody (ANA) and rheumatoid factor (because SS frequently occurs secondary to rheumatoid arthritis), which are associated with autoimmune diseases. Typical autoimmune disease ANA patterns are SSA/Ro and SSB/La, of which SSB/La is far more specific; SSA/Ro is associated with numerous other autoimmune conditions but are often present in Sjögren's (Franceschini and Cavazzana (2005) "Anti-Ro/SSA and La/SSB antibodies," Autoimmunity 38 (1): 55-63).

Autoimmune diseases that can be diagnosed by the methods of the invention include, without limitation, Coeliac disease, diabetes mellitus type 1 (IDDM), lupus erythematosus, systemic lupus erythematosus (SLE), Sjögren's syndrome, Churg-Strauss Syndrome, Hashimoto's thyroiditis, Graves' disease, idiopathic thrombocytopenic purpura, rheumatoid arthritis (RA), ankylosing spondylitis, Crohns disease, dermatomyositis, Goodpasture's syndrome, Guillain-Barré syndrome (GBS), mixed Connective tissue disease, multiple sclerosis, myasthenia gravis, narcolepsy, pemphigus vulgaris, pernicious anaemia, psoriasis, psoriatic arthritis, polymyositis, primary biliary cirrhosis, relapsing polychondritis, temporal arteritis, ulcerative colitis, vasculitis and Wegener's granulomatosis The methods are useful in the diagnosis of a mammal, an animal, or yet further a human patient. For the purpose of illustration only, a mammal includes but is not limited to a human, a simian, a murine, a bovine, an equine, a porcine or an ovine.

In yet another aspect of the above embodiments, the Sjögren's syndrome is an inflammatory autoimmune lacrimal gland disease.

Methods of Treatment

The invention further provides methods of treating subjects having autoimmune disease or likely to develop autoimmune disease, as identified above, or ameliorating the symptoms of autoimmune disease in the subjects. In one embodiment, the method comprises, or alternatively consists essentially of or yet further consists of administering an effective amount of a suitable therapy to the mammal, thereby treating the mammal. Non-limiting examples of suitable therapies include cyclosporin, cevimeline, pilocarpine, a nonsteroidal anti-inflammatory drug, a corticosteroid, an immunosuppressive drug, or a disease-modifying antirheumatic drug. These therapies can be used separately or in combination to treat, or alternatively ameliorate the symptoms of autoimmune disease.

Autoimmune diseases that can be treated by the methods of the invention include, without limitation, Coeliac disease, diabetes mellitus type 1 (IDDM), lupus erythematosus, systemic lupus erythematosus (SLE), Sjögren's syndrome, Churg-Strauss Syndrome, Hashimoto's thyroiditis, Graves' disease, idiopathic thrombocytopenic purpura, rheumatoid arthritis (RA), ankylosing spondylitis, Crohns disease, dermatomyositis, Goodpasture's syndrome, Guillain-Barré syndrome (GBS), mixed Connective tissue disease, multiple sclerosis, myasthenia gravis, narcolepsy, pemphigus vulgaris, pernicious anaemia, psoriasis, psoriatic arthritis, polymyositis, primary biliary cirrhosis, relapsing polychondritis, temporal arteritis, ulcerative colitis, vasculitis and Wegener's granulomatosis Moisture replacement therapies such as artificial tears may ease the symptoms of dry eyes (some patients with more severe problems use goggles to increase local humidity or have punctal plugs inserted to help retain tears on the ocular surface for a longer time). Cyclosporin (Restasis™) is available by prescription to help treat chronic dry eye by suppressing the inflammation that disrupts tear secretion. Prescription drugs are also available that help to stimulate salivary flow, such as cevimeline and pilocarpine. Nonsteroidal anti-inflammatory drugs can be used to treat musculoskeletal symptoms. Corticosteroids or immunosuppressive drugs can be prescribed to ameliorate symptoms. Disease-modifying antirheumatic drugs (DMARDs) such as methotrexate can also be helpful to relieve the patient of the symptoms. Multiple monoclonal antibodies are currently under investigation (Meijer et al. (2007) Clin Rev Allergy Immunol 32 (3):292-7). For patients with severe symptoms, punctal plugs can be inserted into the lower or upper tear drainage canals of the eyes.

In another aspect, the invention provides a method for treating a mammal suffering from or at risk of developing autoimmune disease, comprising administering to the mammal an effective amount of an agent inhibiting the expression or activity of a polypeptide selected from the group Ctss, Ctsh, Ctsr, Ctsw or Ctsz.

In one embodiment, the polypeptide is Ctss. In one aspect of the embodiment, the agent is a Ctss antibody. In one aspect of the embodiment, the agent is a small molecule Ctss inhibitor. Small molecule Ctss and Cts1 inhibitors have been designed and used therapeutically. For example, Katunuma et al. disclosed seven inhibitors of the cathepsin L inhibitor Katunuma (CLIK), one of which also inhibited cathepsin S (Katunuma et al. (1999) FEBS Letters 458:6-10).

Other means of inhibiting protein activity or expression can also be used. Non-limiting examples include siRNA, dsRNA, miRNA, antisense polynucleotide, ribozymes, triplex polynecleotide, antibody and other inhibitory polypeptides.

siRNA, dsRNA, and miRNA to inhibit protein expression can be designed following procedures known in the art. See, e.g., Dykxhoorn, D. M. and Lieberman, J. (2006) Annu. Rev. Biomed. Eng. 8:377-402; Dykxhoorn, D. M. et al. (2006) Gene Therapy 13:541-52; Aagaard, L. and Rossi, J. J. (2007) Adv. Drug Delivery Rev. 59:75-86; de Fougerolles, A. et al. (2007) Nature Reviews Drug Discovery 6:443-53; Krueger, U. et al. (2007) Oligonucleotides 17:237-250; U.S. Patent Application Publication No.:2008/0188430; and U.S. Patent Application Publication No.:2008/0249055.

Delivery of siRNA, dsRNA or miRNA to a cell can be made with methods known in the art. See, e.g., Dykxhoorn, D. M. and Lieberman, J. (2006) Annu Rev. Biomed. Eng. 8:377-402; Dykxhoorn, D. M. et al. (2006) Gene Therapy 13:541-52; Aagaard, L. and Rossi, J. J. (2007) Adv. Drug Delivery Rev. 59:75-86; de Fougerolles, A. et al. (2007) Nature Reviews Drug Discovery 6:443-53; Krueger, U. et al. (2007) Oligonucleotides 17:237-250; U.S. Patent Application Publication No.: 2008/0188430; and U.S. Patent Application Publication No.:2 008/0249055.

Antisense oligonucleotides have nucleotide sequences complementary to the protein coding or "sense" sequence. Antisense RNA sequences function as regulators of gene expression by hybridizing to complementary mRNA sequences and arresting translation (Mizuno et al. (1984) PNAS 81:1966; Heywood et al. (1986) Nucleic Acids Res. 14:6771). An antisense polynucleotide comprising the entire sequence of the target transcript or any part thereof can be synthesized with methods known in the art. See e.g., Ferretti et al. (1986) PNAS 83:599. The antisense polynucleotide can be placed into vector constructs, and effectively introduced into cells to inhibit gene expression (Izant et al. (1984) Cell 36:1007). Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the gene is retained as a functional property of the polynucleotide.

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al. (1991) Science 254:1497) or incorporating 2'-O-methyl ribonucleotides, phosphorothioate nucleotides, methyl phosphonate nucleotides, phosphotriester nucleotides, phosphorothioate nucleotides, phosphoramidates. Another example of the modification is replacement of a non-bridging phosphoryl oxygen atom with a sulfur atom which increases resistance to nuclease digestion. Increased antisense polynucleotide stability can also be achieved using molecules with 2-methyoxyethyl substituted backbones. See e.g., U.S. Pat. Nos. 6,451,991 and 6,900,187.

In another embodiment, ribozymes can be used (see, e.g., Cech (1995) Biotechnology 13:323; and Edgington (1992) Biotechnology 10:256 and Hu et al., PCT Publication WO 94/03596). A ribonucleic acid enzyme ("ribozymes", "RNA enzyme", or "catalytic RNA") is an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. Methods of making and using ribozymes can be found in e.g., U.S. Patent Application Publication No. 2006/0178326.

"Triplex ribozymes" configurations allow for increased target cleavage relative to conventionally expressed ribozymes. Examples of triplex ribozymes include hairpin ribozymes and hammerhead ribozymes. Methods of making and using triplex ribozymes are found in, e.g., Aguino-Jarguin et al. (2008) Oligonucleotides 18(3):213-24 and U.S. Patent Application Publication No. 2005/0260163.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz (1996) Current Opinion in Neurobiology 6:629-634. Another subsequence, the h (hydrophobic) domain of signal peptides, was found to have similar cell membrane translocation characteristics (see, e.g., Lin et al. (1995) J. Biol. Chem. 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

Antibodies may be raised against any portion of a protein which provides an antigenic epitope. Methods to make and use antibodies to inhibit protein function are described in e.g., U.S. Pat. No. 7,320,789 and U.S. Patent Application Publication No. 2009/0010929.

In one aspect of the above embodiments, the Sjögren's syndrome is an inflammatory autoimmune lacrimal gland disease. In another aspect, the mammal is a human patient.

Kits

As set forth herein, the invention provides diagnostic methods for autoimmune disease. In some embodiments, the methods use probes or antibodies specific for a polypeptide selected from the group Ctss, Ctsh, Ctsr, Ctsw, Ctsz, Ifng, Il6ra, Il10, Il10ra, Il15, Tnfa, Apo-F, Lcn-2, lactoperoxidase, lactoferrin or lysozyme. Accordingly, the invention provides kits for performing these methods as well as instructions for carrying out the methods of this invention such as collecting tear and/or performing the screen, and/or analyzing the results, and/or administration of an effective amount of the suitable therapy.

The test samples used in the diagnostic kits can be tears. Methods for preparing protein extracts are known in the art and can be readily adapted in order to obtain a sample which is compatible with the system utilized. A non-limiting illustrative example is the Schirmer's test strip discussed above. In one embodiment, the test strip contains or is embedded with a quantitative substrate that is detectably labeled, such as a fluorometrically labeled antibody, for quantitative detection of the one or more polypeptides identified above.

The kits can include all or some of the positive controls, negative controls, reagents, probes and antibodies described herein for determining the protein expression level or activity level in the subject.

As amenable, these suggested kit components may be packaged in a manner customary for use by those of skill in the art. For example, these suggested kit components may be provided in solution or as a liquid dispersion or the like.

The invention now being generally described, it will be more readily understood by reference to the following examples which are included merely for purposes of illustration of certain aspects and embodiments of the present invention, and are not intended to limit the invention.

Experiment 1

The male NOD mouse is a well-established animal model in which to evaluate the processes of dacryoadenitis and sialoadenitis characteristic of the human disease. This mouse strain spontaneously develops insulin-dependent diabetes mellitus (IDDM) as well as SjS-like disease. Dacryoadenitis, which is more severe than sialoadenitis in this mouse model, is fully-manifested by 12-16 weeks. The manifestations and pathological characteristics of the affected LG in the NOD mouse resemble those changes seen in LG of patients suffering from dacryoadenitis of Sjögren's syndrome. The NOD SCID mouse strain is an immune-incompetent NOD mouse. Prkdc congenic strain can be compared to the NOD mouse to distinguish events associated with inflammation versus events characteristic of the strain that are independent of T- and B-cell mediated inflammatory responses. The NOD SCID strain lacks functional T, B and NK cells, and is free of exocrine tissue destruction.

The early pathological events associated with dacryoadenitis in the NOD mouse and other disease models include the development of functional quiescence (e.g., inability of acinar cells to secrete tear proteins from pre-formed secretory vesicles) in LG regions with otherwise normally-appearing and intact acinar cells, the infiltration of inflammatory cells from ducts into other regions of the LG to form foci, and the damage of extracellular matrix and other acinar cells by factors released from these infiltrating immune cells. Over time, the healthy acinar cell mass in the LG is replaced by lymphocytic foci and regions of necrotic and apoptotic cell debris. Some of the early functional change in otherwise normally-appearing acini have also been linked to exposure to inflammatory cytokines. For instance, it has been shown that IL1α and IL1β, constituents of the inflammatory cytokine milieu, can elicit functional changes in release of neurotransmitters from innervating nerves with the LG responsible for modulation of secretory responses, and may also elicit direct functional quiescence when exposed to acinar cells in vitro. However the factors responsible for triggering the initial autoimmune inflammatory response that contribute to elevated cytokine levels in the LG and then progress to elicit this cycle of damage are still poorly understood.

The Balb/c mouse can also be used as an experimental model. Because this model is induced, one may track disease development, progression and recovery in the female, which more accurately represents the SjS disease demographic in this capacity relative to the NOD model. BALB/c mice recover more quickly from the cytokine injection, within a week, while C57BL/6 mice display a more gradual recovery of within a few weeks. One can start with BALB/c mice. If it becomes necessary to utilize a more expanded time period for analysis, C57BL/c mice can be included. For injection of female mice, aged 10-12 weeks with IL-1, recombinant human IL-1α will be used. Both IL-1α and IL-1β elicit comparable effects in the LG disease model but it is anticipated that it may be possible to secure some IL-1α from the NCI Preclinical Repository to supplement the studies. LG in anesthetized mice can be injected with IL-1α (1 µg) in 2 µL into each LG. Controls can be injected with comparable volumes of saline. Tear fluid collection, tear flow, and corneal, conjunctival and LG integrity and inflammation can be assessed in mice from 1-10 days post-injection.

Materials and Methods

Animals and Animal Procedures:

The NOD and BALB/c mouse colonies were bred in the University of Southern California Vivarium using breeding pairs purchased from Taconic (Hudson, N.Y.) and/or Charles River Laboratories (Wilmington, Mass.). NOD SCID mice were purchased from Harlan (Indianapolis, Ind.). Animals were treated and sacrificed in accordance with policies approved by the University of Southern California Institutional Animal Care and Use Committee. The LG was removed from mice at different ages, after the animals were euthanized by intraperitoneal injection with 55 mg of Ketaject and 14 mg of Xylazine per kg of body weight followed by cervical dislocation. After being removed, LG were either snap frozen and stored in liquid nitrogen for RNA preparation, or fixed immediately with 4% paraformaldehyde and 4% sucrose in PBS for processing and analysis using indirect immunofluorescence.

Reagents and Supplies:

The VersaGene RNA Tissue Kit, originally from Gentra Systems, was later purchased from Thermo Fisher Scientific, Inc. (Fair Lawn, N.J.) under the name 5 PRIME PerfectPure RNA Tissue Kit (FP2302410). All materials and reagents for microarray were purchased from Applied Biosystems (ABI, Foster City, Calif.) through the Vanderbilt Microarray Shared Resources (VMSR, Vanderbilt University, Nashville, Tenn.). All the following materials and reagents for RT and real-time PCR were purchased directly from ABI: the high capacity cDNA RT kit (4368814), TaqMan® universal PCR master mix for real-time PCR (4324018), MicroAmp™ optical 384-well reaction plates (4309849) and Micro-Amp™ optical adhesive films (4311971), and TaqMan® gene expression assays (groups 1 and 2). Group 1 probes include those for the genes of interest including Il1b (Mm01336189_mlor Mm00434228_ml), 116 (Mm_ml), 1110 (Mm_ml), Il15 (Mm00434210_ml), Tnfa (Mm_ml), Infg (Mm_ml), Ctsh (Mm00514455_ml) Ctss (Mm00457902_ml) and Ctsz (Mm00517697_ml). Group 2 probes include those for genes serving as internal controls including Hprt1 (Mm00446968 ml) and Sdha (Mm01352357_ml). Mm followed by 8 digits represents the company assay ID for a TaqMan gene expression assay corresponding to a specific mRNA locus of a gene.

Rat anti-cathepsin H(CATH) monoclonal antibody (MAB1013) and Goat anti-cathepsin S (CATS) polyclonal antibody (3366-100) for Western blotting were purchased from R&D Systems, Inc. (Minneapolis, Minn.) and BioVision, Inc. (Mountain View, Calif.) respectively; goat anti-CATH polyclonal antibody (sc-6497), goat anti-CATS polyclonal antibody (sc-6505), and rat anti-mouse CD14 monoclonal antibody (sc-9150) used for immunofluorescent microscopy were purchased from Santa Cruz Biotechnology, Inc. (Santa Cruz, Calif.). Rat anti-Lamp2 monoclonal antibody (ab13524) from Abcam USA (Cambridge, Mass.);

rat anti-CD68 monoclonal antibody (MCA1957GA) from AbD Serotec USA (Raleigh, N.C.); and Rhodamine Red-X-conjugated donkey anti-goat IgG (705-295-147), FITC-conjugated donkey anti-goat IgG (711-095-152) and FITC-conjugated donkey anti-rat IgG (712-095-150) from Jackson ImmunoResearch Laboratories (West Grove, Pa.) were all used for immunofluorescence analysis. Raw264.7 whole cell lysate was used as the positive control for CATH and CATS proteins analyzed by Western blotting and was purchased from Santa Cruz Biotechnology, Inc. (Santa Cruz Calif., USA). Carbamylcholine (CCH) was purchased from Sigma (St. Louis, Mo., USA).

Fluorescence-Activated Cell Sorter (FACS) Analysis:

FACS analysis was performed on inflammatory cells that were isolated from LG of 12 week old BALB/c, NOD and NOD SCID mice (n=5 mice, pooled) according to a modified protocol as described previously (Schenke-Layland et al., 2008). Inflammatory cell subsets were dual-labeled with the following antibodies: fluorescein isothiocyanate (FITC)-conjugated CD49b/Pan-NK; cyanine-5 (Cy5)-conjugated CD11b (Mac-1) and phycoerythrin (PE)-conjugated Gr1; PE-conjugated B220 and FITC-conjugated CD19; as well as FITC-conjugated CD4 and PE-conjugated CD8. All these antibodies were purchased from BD Biosciences/Pharmingen (San Diego, Calif., USA) and used according to the manufacturer's protocol. Nonspecific isotype-matched Cy5-, PE- and FITC-conjugated IgGs served as controls. Staining with 7-amino-actinomycin (7-AAD; BD Pharmingen, San Diego Calif., USA) was performed to exclude dead cells according to the manufacturer's instructions. Cells were gated properly and a total of 10,000 events were acquired for each sample. All analyses were performed using a BD LSR2 flow cytometer (BD Bioscience, San Jose, Calif., USA). FACS files were exported and analyzed using the FlowJo 8.3.3 software (Tree Star Inc., Ashland, Oreg., USA).

Preparation of Total RNA:

The preparation was conducted using the VersaGene RNA Tissue Kit or 5 PRIME PerfectPure RNA Tissue Kit at room temperature. One to two pairs of LG were taken out from liquid nitrogen, and quickly homogenized on ice using a Brinkman Polytron tissue homogenizer in lysis buffer. The lysate was filtered through a Pre-Clear spin column by centrifugation. The clarified lysate was passed through a purification column by centrifugation. The RNA-bound membrane was treated with DNase I. The RNA was eluted into a collection tube from the column with elution buffer. Three LG RNA samples were pooled from 3 mice in equal amounts for microarray analysis and real-time RT-PCR. Each RNA sample was prepared for real-time RT-PCR from 3-4 pairs of pooled LG when 4-week-old mice were used. All the purified RNA samples were stored at −80° C.

Gene Expression Microarray Analysis:

Triplicates of ABI Mouse Genome Survey Microarray, AB1700 version 1.0.1 (4382672) were used for each group of mice. Each chip was printed with about 33,000 60-mer oligos as probes, representing a complete annotated and curated set of approximately 32,000 mouse genes from the public and Celera databases. The microarray analysis and the sequential data normalization were conducted by VMSR. Before microarray, the purity and integrity of RNAs were confirmed by measurement on an Agilent Bioanalyzer according to manufacturer's manual. In brief, 1 µg of total RNA (about 30 ng mRNA) was used to generate double-stranded cDNA using ABI NanoAmp™ RT-IVT labeling kit (4365715) according to manufacturer's protocol. The entire cDNA product was used in an IVT reaction to generate digoxigenin (DIG)-labeled cRNA. The cRNA was purified using a kit column and assessed for quality on an Agilent Bioanalyzer. All hybridization reagents, hybridization controls, wash reagents, and chemiluminescent reagents were provided in the ABI Chemiluminescence Detection Kit (4342142), and the manufacturer's protocol was followed in the subsequent hybridization procedure. Briefly, the arrays were pre-hybridized with a 1 ml of pre-hybridization mixture for 60 min with agitation at 100 RPM and 55° C. in a hybridization oven. 0.5 ml of fragmented DIG-labeled targets mixed with hybridization controls was added to the pre-hybridization solution. The arrays were continually incubated at 55° C. and agitated at 100 RPM for 16 hr. The arrays were washed and incubated with anti-DIG-AP antibody for 20 min. Following antibody washes, the arrays were incubated with Chemiluminescence Enhancing Solution for 20 min. Substrate for the chemiluminescence reaction was added to each array individually one array at a time. The array was immediately imaged on the 1700 Chemiluminescent Microarray Analyzer. The images were assessed for QA/QC and a primary analysis was completed by the AB1700 Expression Array System Software (v 1.1.1). The raw data were normalized using the ABI quantile-based method and filtered according to the average scores of flags with the analyzer and associated software.

Reverse Transcription (RT) and Real-Time Polymerase Chain Reaction (PCR):

Two reaction steps were carried out with ABI reaction kits and reagents according to the manufacturer's protocols. Briefly, RT reaction was conducted with 1 µg of RNA per 10 µl of reaction volume at 25° C. for 10 min then 37° C. for 2 hr, and terminated at 85° C. for 5 sec, using the high capacity cDNA RT kit. Real-time PCR was conducted using an ABI 7900HT Fast Real-Time PCR System. 1 µl of RT product (diluted with 3.5 µl of nuclease-free $H_2O$), 0.5 µl of the TaqMan Assay Mixture and 5 µl of Universal Master Mix were used in each PCR reaction in a total volume of 10 µl. Triplicates were run for each assay. The samples were preheated at 95° C. for 10 min, followed by 40 cycles of 95° C. for 15 sec and 60° C. for 1 min. The PCR reaction with the TaqMan assay for the house-keeping genes, Hprt1 (hypoxanthine phosphoribosyltransferase 1) or Sdha (succinate dehydrogenase complex, subunit A), were run as internal controls. The recorded data were analyzed using the ΔΔCt study calculating function of the ABI software SDS 2.1. The fold change (FC) for a specific mRNA was obtained by calculations as ΔCt=Ct (studied mRNA)−Ct (house keeping gene mRNA), ΔCt (NOD)−ΔCt (BALB/c)=ΔΔCt, and FC(NOD/BALB/c)=$2^{\Delta\Delta Ct}$.

Confocal Fluorescence Microscopy:

After removal, LG were incubated in PBS containing 4% paraformaldehyde and 4% sucrose at room temperature for 2-3 hr. The gland was transferred to PBS containing 30% sucrose overnight. The glands were embedded into O.C.T. and snap frozen in liquid nitrogen. The blocks were stored at −80° C. prior to tissue sectioning. The blocks were sectioned with a Microm Cryostat (Heidelberg, Germany) into 5 micron thick sections. The slides were incubated with diluted primary antibody in 1% BSA on the top of the tissue section at 37° C. for 1 hr in a moisturized chamber. Sequentially diluted fluorophore-labeled secondary antibodies in 1% BSA and fluorophore-labeled phalloidin (where appropriate) were applied and slides were incubated in the moisturized chamber at 37° C. for 1 hr. Finally, slides were incubated with DAPI in PBS for 5 min, rinsed with water and mounted with water soluble anti-fade mounting medium (Invitrogen, Carlsbad, Calif.) under a cover slip. During the whole procedure, slides were washed with PBS 2-3 times between the treatments. Samples were imaged with a Zeiss LSM 510 Meta NLO confocal/multiphoton imaging system.

Western Blotting with LG Tissue Lysate or Tear Fluid:

Pooled LGs removed from 2-3 mice freshly or stored at −80° C. were homogenized with a motor-driven homogenizer in RIPA buffer (150 mM NaCl, 50 mM Tris-Cl, 0.5% sodium deoxycholate, 0.5 mM EDTA, 0.1% TX-100, 1% NP-40) containing protease inhibitors in a tissue: buffer ratio of 1:5 (w/v). The resulting homogenate was clarified by centrifugation at 10,000 rpm at 4° C. for 10 min. The supernatant was collected and stored at −80° C. An aliquot of the supernatant was mixed with SDS gel loading buffer and heated at 92° C. for 5 min for the subsequent analysis.

For tear collection, the mouse was anesthetized as described above. The mouse LG was exposed by a small incision along an axis defined by the outer junction of the eyelid and the ear, then covered with a layer of fine cellulose mesh (Kimwipe®) cut into a similar size as the gland. The LG was stimulated by adding the agonist carbamylcholine (CCH) (5 µL, 10 µM) onto the mesh on the top of the gland, and tear fluid was collected with glass capillaries at the medial canthus of the eye with care taken not to touch the cornea. Each eye was stimulated two times, in a total collection time of 10 min per eye. The collected tear fluid was transferred from the capillaries to an Eppendorf tube containing protease inhibitors, measured for precise volume, mixed with SDS gel loading buffer, pooled when necessary, and heated at 92° C. for 5 min.

Tissue lysate containing 100 µg of total proteins or 1 µl of tear fluid were loaded to each well and resolved on 10-12% SDS PAGE. The membranes were scanned using a LI-COR Odyssey Infrared Imaging System.

Measurement of enzymatic activity of cathepsins: For activity measurements in LG lysate, freshly collected LG pairs from each individual mouse, either post-stimulation after topical CCH for tear collection or without stimulation, were homogenized with Brinkman Polytron tissue homogenizer on ice in CS Cell Lysis Buffer (1 mg tissue/5 µl buffer) provided in the Cathepsin S Activity Assay Kit™ (Biovision, Inc. Mountain View, Calif.). The same number of NOD and BALB/c mice were used in each experiment. The homogenate was clarified by centrifugation at 10,000×g, 4° C. for 10 min. The resulting lysate was either used immediately or stored at −80° C. for later use.

For activity measurements in tears, mice were anesthetized as described and tear fluid was collected from paired 12-week-old male NOD and BALB/c mice, matched into pairs according to age and sex. The mice were placed resting on their sides under a Motic SMZ-140™ dissection microscope (Xiamen, China). The LG was exposed by a small incision along an axis defined bye the outer junction of the eyelid and the ear and connective tissue capsule enclosing the gland was carefully opened and removed from the upper surface of the gland to which a layer of fine cellulose mesh (Kimwipe™) cut into the shape of the gland but slightly smaller was applied. The ocular surface was washed with AK-Rinse Eye Irrigating Solution™ (Akorn, Abita Spring, La.). The LG was stimulated by adding the agonist CCH (3 µL, 50 µM) topically to the gland and tear fluid was collected by carefully applying a 2 µL, microcaps pipette, (Drummond, Broomall, Pa.) at the medial canthus of the eye, for 5 min. Care was taken not to touch the cornea. Each eye was stimulated with CCH three times, resulting in a total collection time of 15 min per eye. The microcaps were emptied into sterile vials by the aspirator supplied by the manufacturer. The tears collected from both eyes of the same mouse were pooled and immediately analyzed for CATS activity.

CATS activity in LG lysate and tear fluid samples were analyzed using the Cathepsin S Activity Assay Kit™. The collected tear fluid of whole volume from each mouse or 10 µg of LG lysate was diluted to constitute the reaction mixture of 100 µL, with or without inhibitor according to the manufacturer's instructions. The reaction was incubated at 37° C. for 1, 2, and 18 hr. The concentration of resulting fluorescent products was measured using a fluorimeter with 505 nm emission filter. CATH activity was assayed with the Cathepsin H Activity Assay Kit™ (BioVision, Inc.). The procedure was similar to that for CATS activity assay except that only LG homogenate and not tears were analyzed in this assay.

Results

Gene Expression Profiles of Cathepsin Family Members and Other Inflammatory Factors in LGs of NOD and BALB/c Mice.

Severe extracellular matrix degradation and immune cell infiltration are prominent features of LGs in male NOD mouse LG aged 12-18 weeks. Cathepsins are a major category of proteases responsible for regulation of extracellular matrix; in fact one of their roles as tear secretory proteins is to regulate extracellular matrix homeostasis. Gene expression profiles were analyzed to determine possible alterations in their expression in male NOD mouse LG, using gene expression microarray analysis to investigate if cathepsin family members contributed to these pathologic events associated with immune cell infiltration. The results are presented in Table 1. The hybridization signals for mRNAs of cathepsins H (Ctsh), R (Ctsr), S (Ctss), W (Ctsw), and Z (Ctsz) were elevated in the LG of NOD mice compared to the BALB/c controls. There was no difference for the rest of the cathepsin family members except cathepsin K (Ctsk) which showed expression that was 40% as high as the BALB/c control.

Macrophage-expressed cytokines and their receptors were also examined for their mRNA levels in the LGs of NOD mice relative to the BALB/c controls. However, only a subset of these cytokines and receptors were detected by microarray due to the relative insensitivity of this technique to low abundance mRNAs as shown in Table 2. The mRNA levels of interferon-γ, interleukin-10 receptor α and tumor necrosis factor α were clearly also higher in the LGs of male NOD mice than that of matched BALB/c mice.

Data Validation and Expanded Investigation of Gene Expression.

The results of microarray were validated by real-time RT-PCR which evaluated the expression levels of cathepsin family members and cytokines of interest. Beside the total RNAs from the LGs of 12-week-old male NOD and BALB/c mice, total RNAs from age matched NOD SCID mice.

TABLE 1

Differentially expressed cathepsin family members in LGs of NOD mice versus BALB/c mice characterized by microarray analysis

| Gene | NCBI Accession | FC (NOD/BALB) | P Value | Change in NOD |
|------|----------------|---------------|---------|---------------|
| Ctsb | BC006656 | 1.0 | 0.3330 | no change |
| Ctsc | NM_009982 | 1.2 | 0.0624 | no change |
| Ctsd | NM_009983 | 1.0 | 0.3311 | no change |
| Ctsf | NM_019861 | 0.7 | 0.0006 | no change |
| Ctsh | NM_007801 | 2.1 | 0.0015 | increase |

TABLE 1-continued

Differentially expressed cathepsin family members in LGs of NOD mice versus BALB/c mice characterized by microarray analysis

| Gene | NCBI Accession | FC (NOD/BALB) | P Value | Change in NOD |
|---|---|---|---|---|
| Ctsk | NM_007802 | 0.4 | 0.1128 | may decrease |
| Ctsl | NM_009984 | 0.9 | 0.4897 | no change |
| Ctso | NM_177662 | 1.4 | 0.1111 | no change |
| Ctsr | NM_020284 | 6.9 | 0.0015 | increase |
| Ctss | NM_021281 | 4.4 | 1.7E−07 | increase |
| Ctsw | NM_009985 | 3.1 | 0.0230 | increase |
| Ctsz | NM_022325 | 1.8 | 0.0029 | may increase |

FC represents the fold change obtained by comparing the hybridization signal of NOD mouse LG to the signal from BALB/c mouse LG (NOD/BALB/c) after normalization. The full names for the gene symbols listed in this table are: Cts(letter), genes for cathepsin family members.

TABLE 2

Increased mRNA levels of cytokines and proinflammatory factors in LG from NOD versus BALB/c mice characterized by microarray analysis

| Gene | NCBI Accession | FC (NOD/BALB) | P Value | Change in NOD |
|---|---|---|---|---|
| Ifng | NM_008337 | 14.5 | 1.2E−06 | increase |
| Il1b | NM_008361.3 | — | — | under detection |
| Il6 | NM_031168.1 | — | — | under detection |
| Il6ra | NM_010559 | 2.6 | 0.1740 | may increase |
| Il10 | NM_010548 | 2.6 | 0.0636 | may increase |
| Il10ra | NM_008348 | 6.1 | 0.0014 | increase |
| Il15 | NM_008357 | 1.8 | 0.3883 | may increase |
| Tnfa | NM_013693 | 4.6 | 0.0003 | increase |

FC represents the fold change obtained by comparing the hybridization signal of NOD mice to the signal of BALB/c mice (NOD/BALB/c) after normalization.

TABLE 3

FACS analysis of inflammatory cells isolated from LGs of BALB/c, NOD and NOD SCID male mice.

| Lineage Marker | BALB/c | NOD | NOD SCID |
|---|---|---|---|
| B220+ CD19− | 6.8% | 3.9% | 5.1% |
| B220+ CD19+ | 4.1% | 34.0% | 0.8% |
| CD4+ CD8− | 3.1% | 13.0% | 3.1% |
| CD4− CD8+ | 2.1% | 7.9% | 2.0% |
| CD11b+ GR1− | 7.0% | 25.0% | 11.0% |
| CD11b+ GR1+ | 2.0% | 3.5% | 1.7% |
| CD11b− GR1+ | 4.2% | 6.9% | 3.0% |
| Pan-NK | 3.6% | 5.9% | 2.2% |

5 male mice of each strain each aged 12 weeks were used for LG collection and isolation of interstitial inflammatory cells as previously described. B220+ CD19−, characterized as early B lymphoid progenitor cell; B220+ CD19+, B lymphoid progenitor cell; CD4+ CD8−, mature T helper cell; CD4−CD8+, mature cytotoxic T cell; CD11b+GR1—, macrophage; CD11b+GR1+, myeloid immunoregulatory cell; CD11b− GR1+, granulocytes; Pan-NK, NK cell. Percentage of each cell lineage was obtained by the cell number of a specific cell subset divided by total cell counts analyzed, then multiplied by 100%.

Female NOD and BALB/c mice, and 4-week-old NOD and BALB/c mice of both genders were also analyzed concomitantly. The results are summarized in FIG. 1. The expressions of the cytokines which were not detected by microarray, possibly due to low abundance, were also re-evaluated by this method. Consistent with the microarray analysis, the mRNA levels of Ctsh, Ctss and Ctsz in the 12 week old male NOD mouse LG were markedly higher than in the BALB/c mice as shown in FIG. 1A; all the macrophage-produced cytokines tested also showed markedly increased expression in the LG of NOD mice to different extents as shown in FIG. 1C. Interestingly, the mRNAs levels of the obesity-induced proteins Ctsh, Ctsz, Ctss, 11-6 and INF-α were all higher in NOD SCID mice than in BALB/c mice although the levels in NOD SCID mice were still lower than those detected in NOD mice (FIG. 1A); NOD SCID mice, like NOD mice, exhibit notable lipid deposition in the LG of the male mice. 11-10 was the only gene which exhibited equivalent elevated expression between male NOD and NOD SCID mouse LG (FIG. 1C). Comparison of gene expression levels in mice aged 4 weeks showed little to no changes in these same markers (FIGS. 1B and 1D). This age of 4 weeks is prior to the onset of lipid deposition and accumulation.

Macrophages are Prominent Infiltrating Cells in Diseased LG.

A previous study has revealed the presence of various types of infiltrating immune cells including macrophages, neutrophilic and eosinophilic granulocytes, B-cells and T-cells within the LG of NOD mice at 18 weeks of age. The expression profiles of cathepsins and cytokines by real-time RT-PCR measured here also suggested the activation of macrophages in NOD mouse LG. To understand the role macrophages play in this inflammatory autoimmune disorder in this disease model, lineage classification was performed by FACS analysis with prepared immune cell populations from pooled LGs from 12-week-old male NOD, NOD SCID and BALB/c mice. Proportions of B-cells (B220+ CD19+), T-cells (CD4+ and CD8+), macrophages (CD11b+) and other immune cells out of the whole immune cell population counted in the LGs of three strains are listed in Table 3. The result showed that macrophages constitute a major population (25%), the second large population after the B cells in NOD mouse LG. NOD SCID mice lack T and B cells and have only partial competence in the function of myeloid cells. Consistent with this, there were significantly low numbers of B-cells (B220+CD19+) and T-cells (CD4+ and CD8+) detected from NOD SCID mouse LG compared to that from NOD mice. The numbers of these cell types were even lower than that from BALB/c mouse LG; on the other hand, the macrophage population within the LG of NOD SCID mice was increased to 11% in contrast to 7% in the LG of BALB/c mice. This number was still lower than that in matched NOD mouse LG due to the lack of stimulation by and communication with lymphocytes.

Characterization of CATS Protein Distribution in LG within Macrophages and Acinar Cells.

Figure 2:
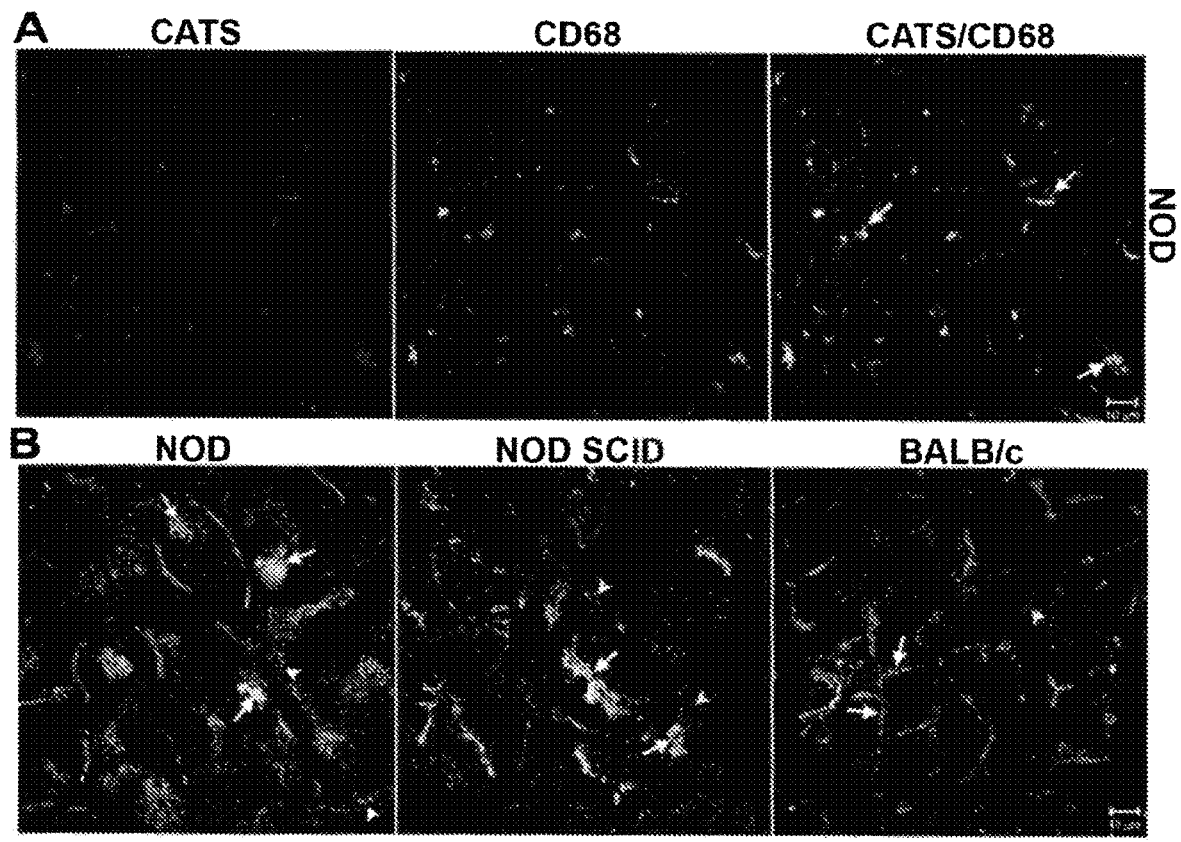
FIGS. 2A and 2B show the detection of CATS in different locations in LG from different mouse strains. Cryosections of LGs from 12-week-old male NOD, NOD SCID and BALB/c mice were incubated with goat anti-mouse CATS polyclonal antibody and rat anti-CD68 monoclonal antibody followed by appropriate fluorophore-conjugated secondary antibodies. The sections were imaged by confocal fluorescence microscopy. Nuclei were stained with DAPI and actin filaments with Alexa Fluor 647 in all panels to delineate the relative cellular location of the positive signals. Arrowheads point to CATS-positive cells in the surrounding region of the LG; arrows to CATS-positive cells in the interior region of the LG; hollow arrowheads to CATS- and CD68-positive cells in the surrounding region of the glands; and arrows to CATS and CD68-double positive cells in the interior region of the gland. Bars=10 μm

Previous studies demonstrated that CATS participates in both antigen presentation and normal cellular protein turnover and also degrades extracellular matrix in cancers. The extensive extracellular matrix degradation and immune cell infiltration combined with the gene expression profiling result from the current study indicated that the increased expression of CATS may directly contribute to LG destruction by degrading the extracellular matrix or alternatively that it may indirectly contribute to LG destruction by stimulating neoautoantigen presentation and consequent lymphocyte proliferation. Hence, the localization and abundance of CATS protein in LG was investigated using immunofluorescence microscopy. The results showed that CATS was present in populations of CD68-positive and -negative infiltrating cells (FIG. 2) within the LG. It was also noted that the distribution pattern of CATS was very similar to that of CATH. Both CATS-positive cells were within the connective tissues surrounding the LG of the all three strains, whereas CATS-enriched cells in the interior region of the gland were only detected in LG from NOD and NOD SCID mice. Additionally, CATS-positive cells were seen among the lymphocytic foci in the LG of NOD mice.

Figure 3:
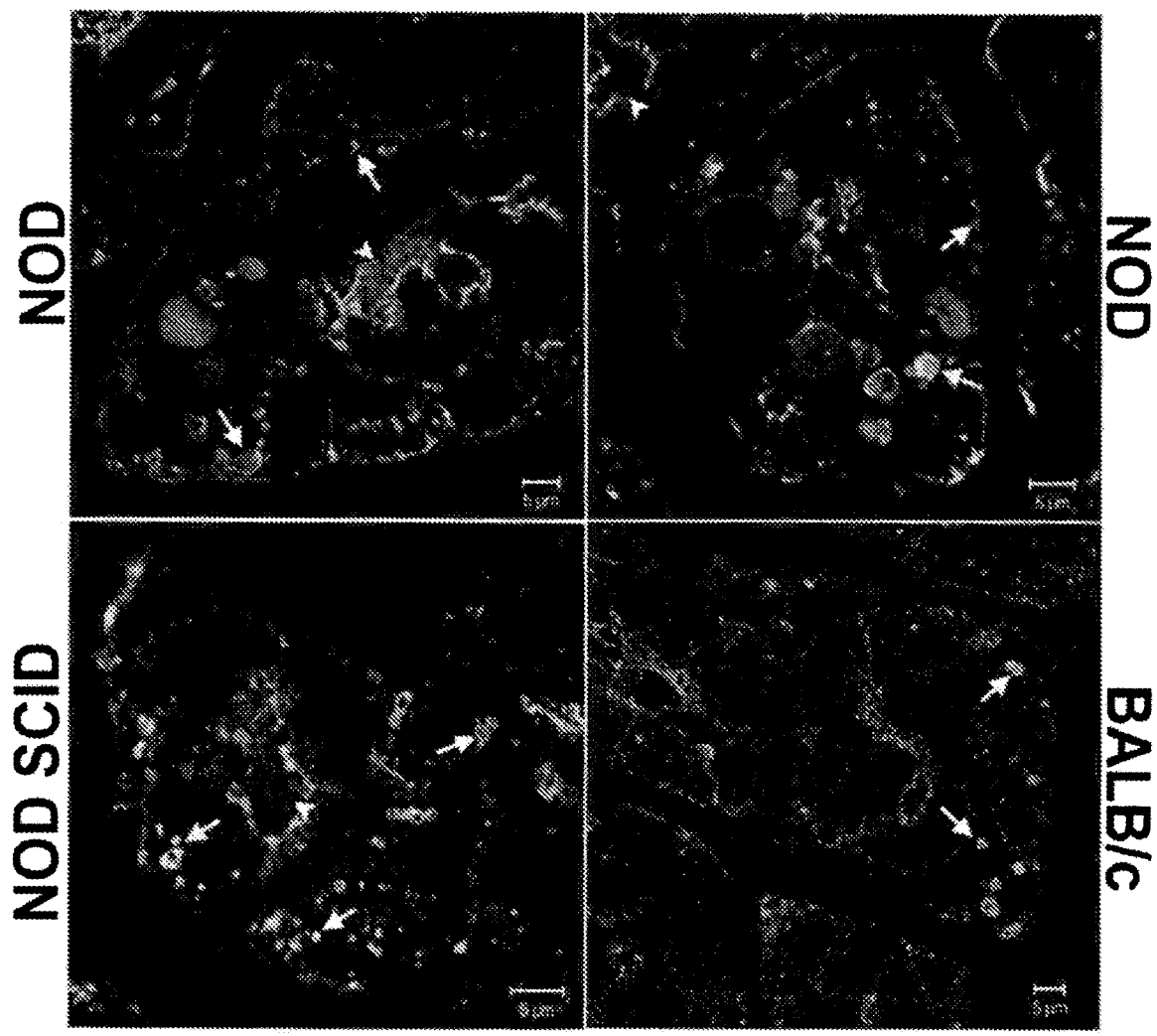
FIG. 3 illustrates the redistribution of CATS protein in LG acinar cells from NOD and NOD SCID mice. Cryosections of LGs from 12-week-old male NOD, NOD SCID and BALB/c mice were incubated with goat anti-mouse CATS polyclonal antibody and rat anti-Lamp2 monoclonal antibody followed by appropriate fluorophore-conjugated secondary antibodies. The sections were imaged by confocal fluorescence microscopy. Lamp2-enriched vesicles marked late endosomes/lysosomes. Labeling with DAPI for nuclei and Alex Fluor 647 for actin filaments was conducted to delineate the relative location of the targets. Arrowheads point to the CATS-positive areas; arrows to the Lamp2-positive areas. Bars=10 μm.

CATS immunofluorescence was also detected within the acinar cells in addition to the macrophage and the other cell types described above. The number and size of Lamp2-positive late endosomes/lysosome and the abundance of the CATS protein appeared to be markedly increased in acinar cells from NOD (FIG. 3A) and NOD SCID (FIG. 3B) mice relative to the amounts in acinar cells from LG from matched BALB/c mice (FIG. 3C). CATS was also detected in the organelles in the subapical region surrounding the lumen of acinar cells from NOD (FIG. 3D) and NOD SCID (FIG. 3E) mice in contrast to the solely basolateral punctate labeling for CATS in the acinar cells from BALB/c mice (FIG. 3F).

Increased Abundance and Activity of CATS in NOD Mouse LG Lysates and Tears.

Figure 4:
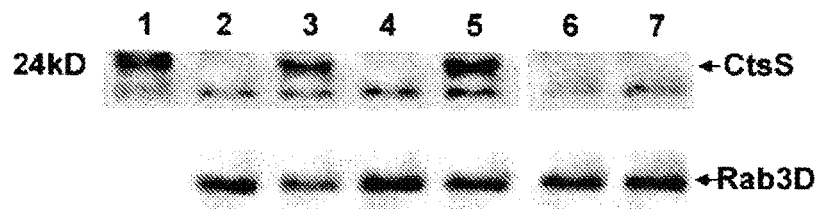
FIGS. 4A and 4B show comparison of CATS abundance and activity of LG between NOD and BALB/c mice. A: Western blotting to compare the protein abundance of CATS. LG lysates were prepared from 12-week-old male NOD mice or matched BALB/c mice. 100 μg each of LG lysates was loaded in each well of a 11% SDS-polyacrylamide gel. 50 μg of Raw264.7 cell lysate was run in parallel as a positive control. The proteins transferred to nitrocellular membrane were hybridized with goat anti-CATS polyclonal antibody. One of the two membranes prepared in parallel was hybridized with rabbit anti-Rab3D antibody as a loading control; this protein is highly abundant in LG. B: CATS activity assay. Right: 10 μg each of paired LG lysates from the two strains were incubated for 1, 2 and 18 hours and the fluorescence of the products was measured at excitation/emission wave lengths of 400/505 nm. The enzymatic activity is expressed as fluorescent units; error bars show SEM. Left: Assays were conducted as described with the addition of CATS inhibitor to the reactions to verify the specificity of the enzyme in the LG lysates.
Figure 4:
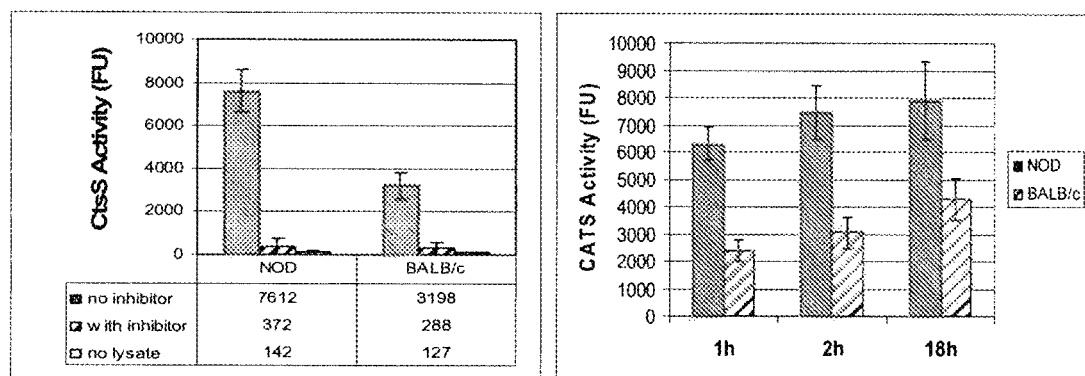

The increased copy number of Ctss mRNA, the detection of additional CATS-positive cells in NOD mouse LG, and the detection of increased CATS immunofluorescence within subapical compartments in acinar cells described above all suggest an increased protein abundance and catalytic activity of CATS in LG under these pathological conditions. The CATS abundance was thus compared in LG of NOD mice to that of BALB/c mice by Western blotting analysis (FIG. 4A). Consistently, a clear 24 kD MW protein band corresponding to the molecular weight of active form of CATS in the gland lysate from NOD mice was detected (4A) but a much weaker to no band at the same position in LG lysate from BALB/c mice (4A). Enzymatic activity assays were also conducted for comparison of the CATS activities in LG between the two strains (FIG. 4B). The result showed the average CATS activity from NOD mouse LG lysates was significantly greater than that from the control BALB/c mice LG lysates.

Figure 5:
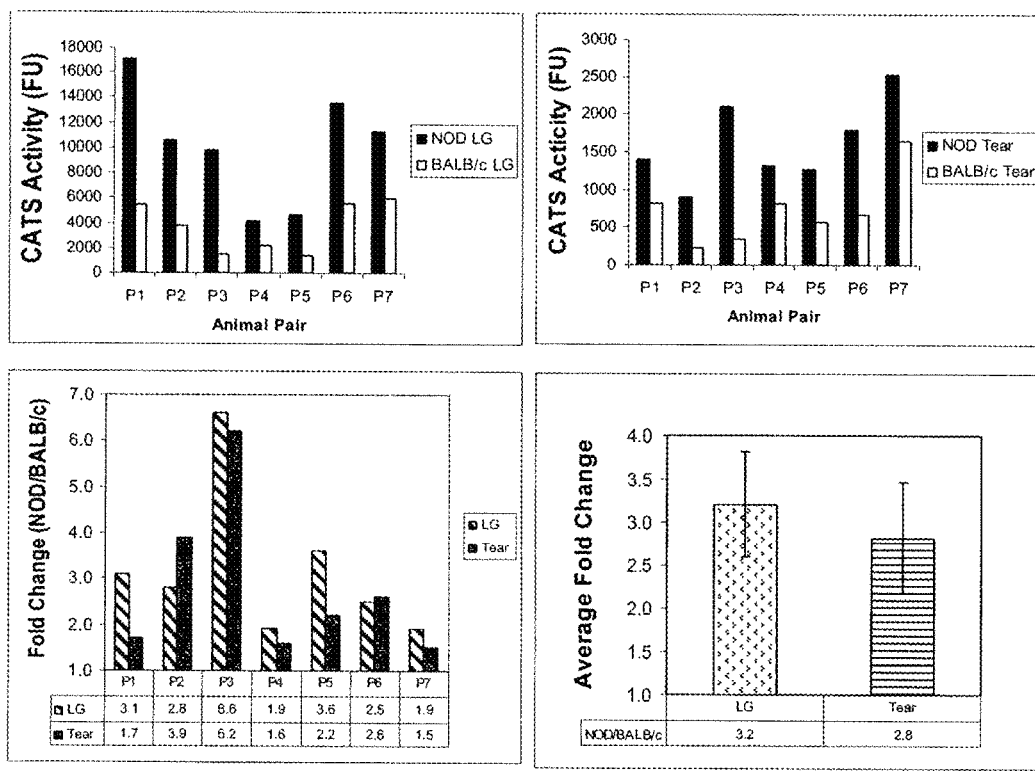
FIGS. 5A and 5B show comparison of CATS enzymatic activities from stimulated LG lysates and tear fluid between NOD and BALB/c mice. Mice were anesthetized and tear fluid collected following stimulation with CCH as described in Materials and Methods. Catalytic activity was assayed in the absence or presence of the specific CATS inhibitor used in FIG. 4. A: CATS activity in stimulated glands and average fold change values based on pairwise comparisons. B: CATD activities in stimulated LG and tears between the paired NOD and BALB/c mice. Errors depict SEM.
Figure 5:
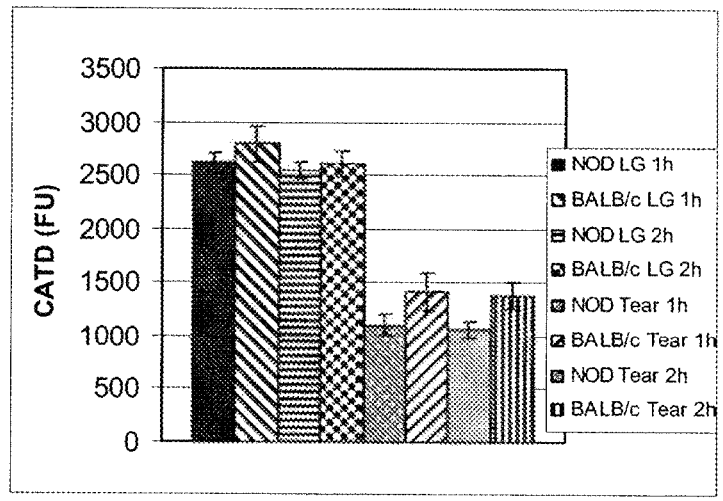

The evident redistribution of CATS immunofluorescence into apparent subapical secretory vesicle-like organelles as well as within the lumena in the acinar cells suggested that CATS may be actively secreted at the apical membrane into the tear fluid in NOD mice. Hence the enzymatic activities of the tears were measured in the absence or presence of specific inhibitor, in parallel with the LG lysate. The results demonstrated significantly higher CATS activities in tear fluid of NOD mice relative to those of BALB/c mice upon stimulation of the LG with the agonist, CCH (FIG. 5). Consistent with the testing results from LG lysates, the average enzymatic activity of the tears collected was measured from the stimulated glands of NOD mice versus from that of BALB/c mice.

Cathepsin D, like CATH and CATS, is another member of peptidase C1 family expressed in LG (Table 1). Using this activity as a control activity with expression unchanged in the NOD strain relative to the BALB/c strain, no differences in either catalytic activities or gland lysates or tears was detected between the two mouse strains, consistent with the result of the microarray (FIG. 5C).

Characterization of CATH Protein within Macrophages but not Acinar Cells in LG.

Figure 6:
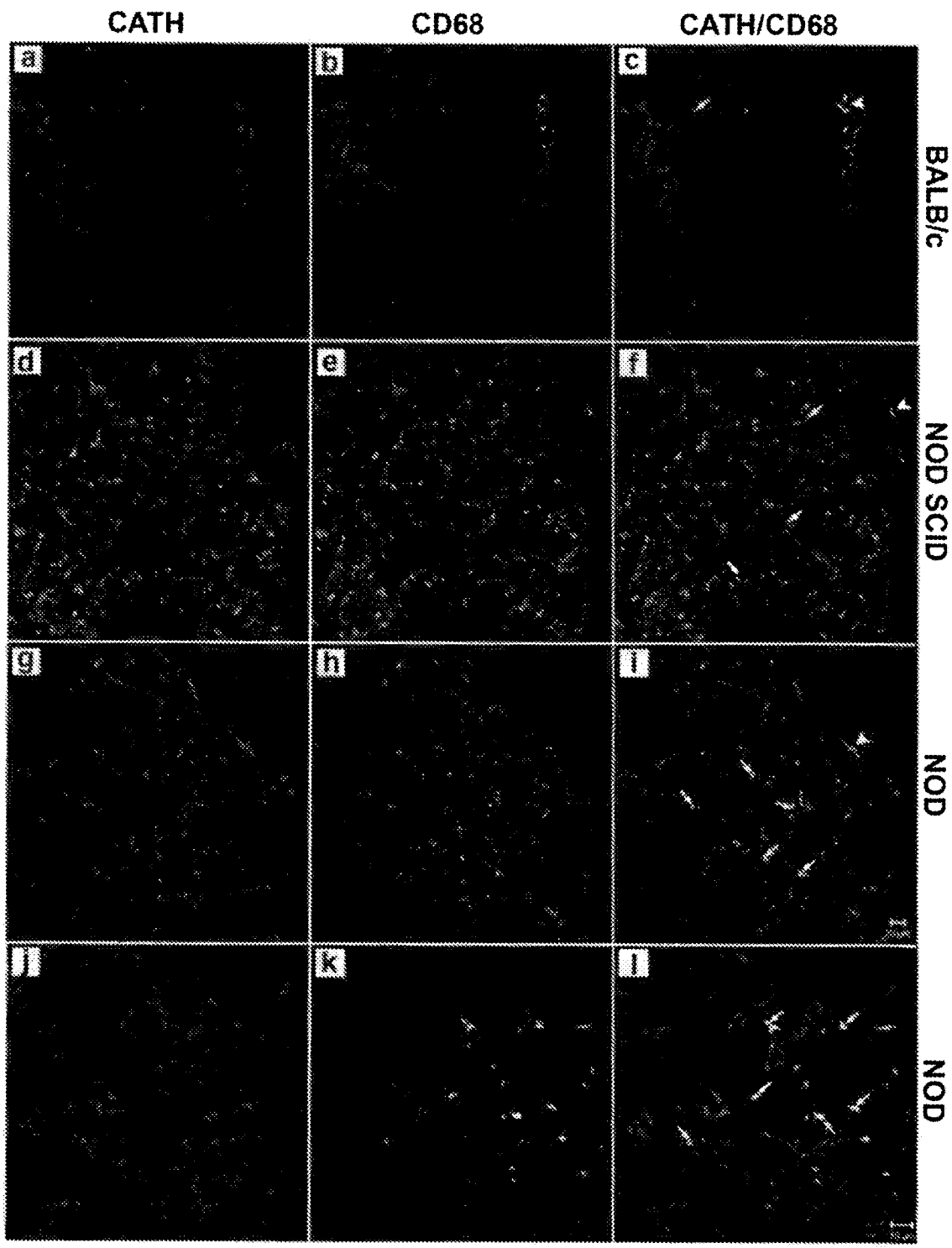
FIGS. 6A through 6L show detection of CATH positive cells in different locations in LG from different mouse strains. Cryosections of LG from 12 week male NOD, NOD SCID and BALB/c mice were incubated with goat anti-CATH polyclonal antibody and rat anti-CD68 monoclonal antibody followed with fluorophore-conjugated secondary antibodies. The sections were imaged by confocal fluorescence microscopy. CATH and CD68-enriched macrophages labeling are shown separately in the indicated columns as well as in the overlay image. All panels were also labeled to detect nuclei (DAPI-labeled) and panels A-I were additionally labeled for actin filaments. Parenchymal tissues and surrounding regions of LG are presented in panels A-I and while infiltrating foci are magnified in panels J-L. Arrowheads point to CATH and CD68 double positive cells in the surrounding region of the LG (C, F and I); arrows to the double positive cells in the interior region of the LG (C, F, and I) or in the infiltrating foci (L). Panels a-i share the same magnification and the magnification bar for these figures is 20 µm, as shown in I. Panels J-L share the same magnification and the magnification bar for these figures is 10 µm, as shown in L.

CATH is defined as an aminopeptidase (notably, cleaving Arg-l-Xaa bonds) as well as an endopeptidase. Its cellular function is somewhat obscure to date. Its mRNA was markedly elevated in the NOD mouse LG. Immunofluorescent microscopy was performed to localize the cells producing CATH protein. The results are shown in FIG. 6. Similar to the distribution of CATS, the CATH protein was observed in some cells in interstitial and elastic tissue within the sac surrounding the LG in NOD, NOD SCID and BALB/c mice (FIGS. 6A, D and G). The CATH-positive cells were also enriched at the intercellular space between the acini from NOD and NOD SCID mice but not from BALB/c mice (FIGS. 6F and I). In addition, CATH-positive cells were observed among the infiltrating foci in the LG of NOD mice (I). Some but not all CATH-positive cells were also positive for CD68 and these cells were seen either at the extracellular space or within the foci (FIG. 6C, K, L). Unlike CATS, no CATH protein was detected in the acinar cell.

Figure 7:
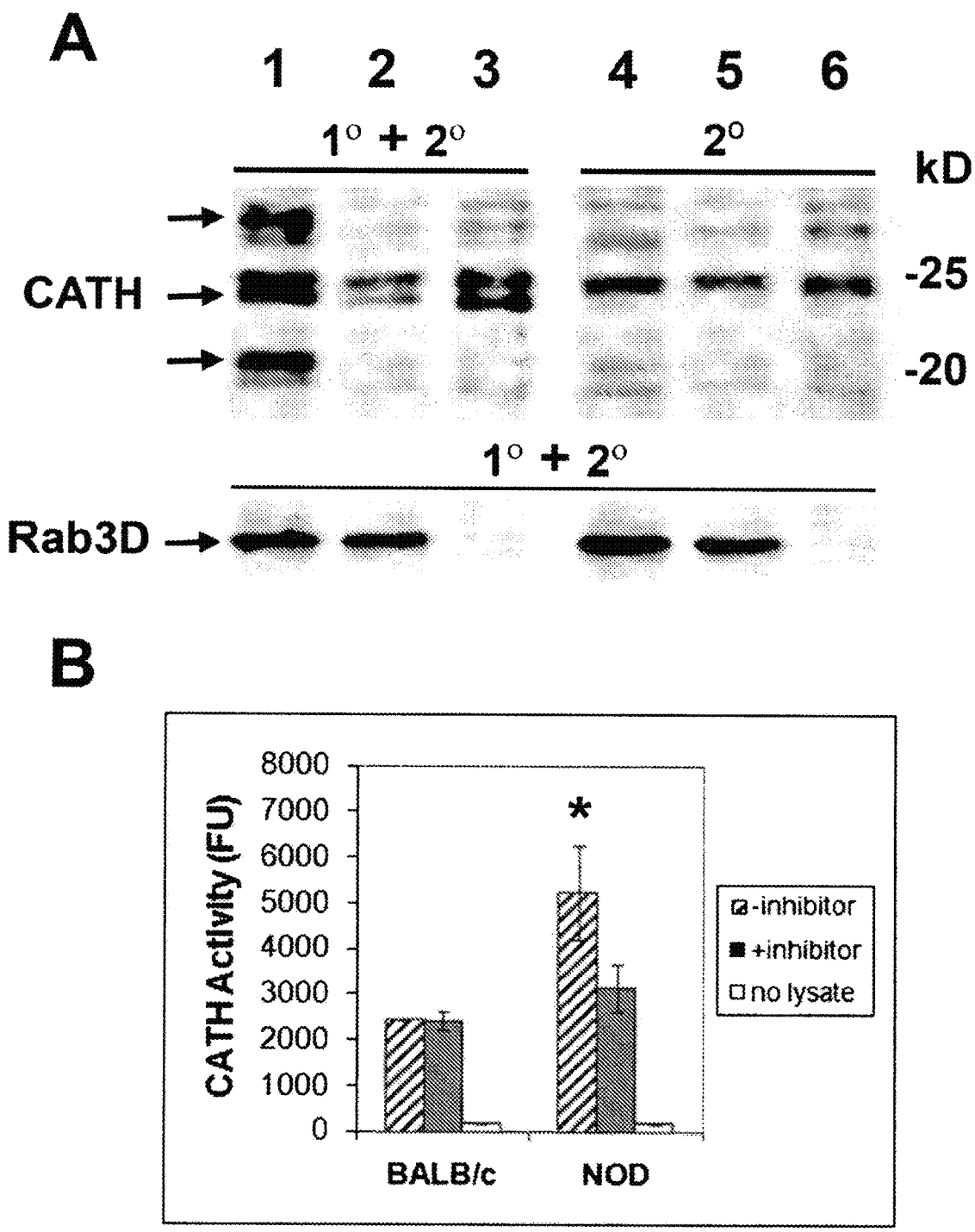
FIGS. 7A and B illustrate the comparison of CATH abundance and activity in LG lysates from 12-week old NOD and BALB/c mice. A: Western blotting to compare the protein abundance. 100 µg of lysate prepared from NOD mouse LG (lanes 1 and 4), 100 µg of lysate prepared from BALB/c mouse LG (lanes 2 and 5) and 30 µg of Raw264.7 cell lysate (lanes 3 and 6) were loaded onto an SDS-polyacrylamide gel. Upper panel: The proteins transferred to nitrocellulose membranes were blotted with rat anti-CATH monoclonal antibody with (1°+2°, lanes 1-3) or without (2°, lanes 4-6) primary antibody, then with IRDye 800-conjugated secondary antibody (lanes 1-6). Lower panel: The same membrane after being stripped was re-blotted with rabbit anti-Rab3D polyclonal antibody and secondary antibody (1°+2°, lanes 1-6) as a loading control. Major CATH bands are marked by arrows and correspond to the single chain of one of the active forms at 27-28 kD and the heavy chain of the other active form at 23-24 kD (co-migrating with the positive control), as well as a possibly proteolyzed or truncated species at 20 kD. These bands are most abundant in NOD mouse LG lysate. A band above the specific 23-24 kD band in lanes 1-3 is visible due to non-specific reactivity of all samples with the goat anti-rat secondary antibody (see lanes 4-6). The molecular weights marked indicate the migration of the molecular weight standards. B: CATH activity assay. 10 µg each of paired LG lysates (n=3) were incubated with substrate in the absence (−inhibitor) or presence (+inhibitor) of inhibitor. Samples labeled "no lysate" are the reaction background. Accumulated fluorescence of products from LG lysates was measured at 2 h. Activity is fluorescence units (FU) per 10 µg lysate. Errors are ±SEM and *, $p<0.05$.

Western blotting analysis was conducted to investigate if the abundance of CATH protein also increased in parallel with the elevated mRNA levels in NOD mouse LG. The result showed that there were two protein bands recognized by the anti-CATH antibody with approximate molecular weights of 37 and 27 kD, corresponding to the full length protein and the active cleaved form of CATH, respectively (FIG. 7A). The abundance of CATH, especially the active form, was significantly higher in the lysates of LGs from NOD mice than from BALB/c mice.

The enzymatic activity of CATH was also determined as shown in FIG. 7B. Significantly elevated catalytic activity of the enzyme was detected in LG lysates from 12-week-old male NOD mice versus that from the matched BALB/c mice. Applicants noted that CATH remained catalytically active for an extended period of time, especially in the assay with NOD mouse LG lysates, in comparison to CATS and CATD. Additionally, the catalyzing activity was only partially inhibited by the CATH inhibitor (right panel), indicating a likely contribution of the partial activity by other non-CATH enzyme(s) or limited inhibitory ability of the inhibitor.

DISCUSSION

The experiment described above reports, for the first time, the significant upregulation of CATS expression and activity in the LG during development of autoimmune inflammatory disease. Applicants' data further suggests, as specified below, that CATS expression is upregulated in both the infiltrating immune cells as well as in the acinar cells that constitute the bulk of the gland, suggesting a complex role for CATS in etiology of disease.

Consistent with gene expression analysis, CATS-positive cells are detected more abundantly in the NOD mouse LG than in the BALB/c mouse LG. CATS protein was detected in a vast number of the infiltrating cells in the NOD mouse LG within foci as well as at the LG periphery, but was only detected in some macrophage-like cells in the peripheral connective tissue-enriched areas of the BALB/c mouse LG. While many of the CATS-enriched cells within inflammatory cell foci in the NOD mouse LG were CATS+/CD68+, confirming their identity as macrophages, a considerable number of CATS-positive cells were CD68-negative, suggesting the presence of other antigen presenting cells (APC). Additionally, a notable proportion of CATS positive cells were extremely lysosome rich as evidenced by their enrichment in Lamp2 staining. These observations are consistent with previously established mechanisms for the role of CATS in antigen presentation and cellular protein maturation in macrophages and other APCs, which contribute to activation of T-, B- and other lymphocytes.

Beside the CATS-positive immune cells, CATS immunofluorescence and, by extension, protein abundance was also significantly increased in the acinar cells from NOD and NOD SCID mouse LG versus that from BALB/c mice. The acinar cells constitute approximately 85% of the cell mass of the LG and are largely responsible for production and release of secretory proteins into the tears. They therefore maintain an abundant array of mature secretory vesicles within their subapical cytoplasm. A subset of CATS-enriched organelles within the acinar cells was significantly co-localized with markers within the acini. These findings suggested stimulated biogenesis of lysosomal-like organelles in acini from NOD mouse LG. A subset of CATS was also detected within very large secretory vesicle-like organelles localized in the sub-apical region, as well as within the lumena of the acini of NOD and NOD SCID mice, but not in the acini of BALB/c mice, indicating altered protein sorting and apical secretion for CATS in the NOD background. This finding was verified, in the NOD mouse, by the detection of increased CATS activity in tears relative to the BALB/c control strain. Routinely, newly synthesized lysosomal proteins such as CATS are processed in the endoplasmic reticulum (ER) and Golgi apparatus to the trans-Golgi network (TGN), then are actively sorted to lysosomes via late endosomes as the terminal destination. This sorting path appears to be partially altered in NOD mouse with a diversion of some of the upregulated CATS into the regulated apical secretory pathway. This missorting may arise from one of two possibilities: 1) CATS overproduction may saturate the normal sorting pathways in the TGN such as mannose-6-phosphate receptors and others that sequester lysosomal proteins into cargo vesicles destined for lysosomes, and thus the extra CATS may traffic through a default pathway into mature secretory vesicles; 2) CATS may be actively missorted into this path due to a fundamental abnormality in the cellular trafficking system of NOD (and NOD-SCID) mice.

While CATD is known to be an established lysosomal resident protein, it is also known to be a component of normal tear fluid, consistent with Applicants' unpublished proteomic data in the mouse. Gene expression microarray showed no change in CATD expression at the mRNA level, and the corresponding enzymatic analyses showed no changes in either LG tissue or tears from NOD mice compared to the control, despite the significant elevation of CATS activity. Therefore it appears that CATD is not involved in nor influenced by the disease progression in NOD mouse LG. This result is supportive of the theory that the intracellular sorting of lysosomal proteins is regulated by the abundance of each respective protein, since only the upregulated CATS and not the normally-expressed CATD are missorted to secretory vesicles. However, membrane trafficking is highly dependent on lipid membrane composition, and lipid-enriched subdomains or "lipid rafts" are known to serve as signaling platforms and to mediate specific internalization events such as caveolar endocytosis, so an alternative theory is consistent with the lipid metabolic abnormalities in the acinar cells from NOD mice, particularly if different sorting processes are involved in capture of CATD and CATS to lysosomes. Regardless of cause, this collective observations of increased lysosomal abundance in parallel with missorting of lysosomal proteins into the regulated secretory pathway effect demonstrates global changes in protein sorting and processing within the acinar cells that may contribute significantly to pathology. The increased CATS and lysosomal activity suggests enhanced and possibly abnormal protein degradation and processing which may enhance CATS production of neoautoantigens in the altered lysosomal pathway of the acinar cells, while enhanced CATS activity in tears may result in tear protein degradation and also extracellular matrix damage to the ocular surface.

In addition to CATS, the spectrum of upregulated inflammatory cytokines that accompany CATS upregulation in obesity were also detected in the NOD mouse LG. Without being bound by theory, Applicants hypothesize that these cytokines are largely produced by infiltrating macrophages, based on the following reasoning. The LG of NOD SCID mice still retains macrophages at an increased number relative to BALB/c mice although not as many as in the NOD mice, while it lacks T and B lymphocytes. In parallel, increased mRNAs of Tnfa, Il6 and Il10 were detected in NOD SCID mouse LG relative to BALB/c mice although to a less extent compared with NOD mice. These results suggest that the macrophages present in the LG of NOD mice, compared to NOD SCID mice, are further stimulated by lymphocytes resulting in the increase in their number in parallel with the more vigorous inflammatory response.

CATH protein, also significantly upregulated in NOD mouse LG relative to BALB/C mouse LG, was exclusively detected in non-acinar cells including cells migrating into the extracellular space between acini as well within infiltrating foci. Applicants also noted a corresponding increase in CATH enzymatic activity within NOD LG lysates. Persistent conversion of the substrates into products in the proteolytic activity assay during an 18 hr extended time course indicates that CATH has a stable and long lasting activity in vivo compared to CATS. Partial co-localization of CATH immunofluoresence with that of CD68 indicates some of CATH-positive cells are macrophages. The physical locations of CATH suggest its involvement in macrophages and other inflammatory cell functions. Previous studies reported that this enzyme is secreted from neutrophils and participates in the degradation of extracellular matrix. The extensive loss of extracellular matrix within the NOD mouse LG that has previously been reported thus renders CATH a candidate for this pathological event in the NOD mouse model.

The increased protease activity of CATS and CATH within the LG has multiple possible consequences. First, the increase in CATS-enriched lysosomes labeled with Lamp2 suggests that lysosomal degradative capacity may be enhanced, thus raising the possibility that protease degradation of proteins in lysosomes becames abnormal. Previous work has suggested that alterations in proteolytic activity may expose cryptic epitopes on otherwise tolerated self-proteins, which may be effluxed or recycled into the interstitium from the late endosomal compartments where they may encounter increased CATS. Cryptic epitopes in the interstitium may encounter primed APC and macrophages, thus potentiating autoimmunity. Likewise, CATS activity on the ocular surface and CATH activity within the tissue may promote loss of extracellular matrix in the ocular surface system.

The detection of proteolytic activity of CATS in the tear fluid of NOD mouse in parallel with the detection of CATS immunoreactivity in subapical secretory vesicles shows that this enzyme is secreted from acinar cells. This fact suggests the possibility that the CATS in tears may digest certain protein components of the cornea, therefore damage the integrity of the ocular surface as well as enhancing sensory input from the cornea to the LG, an event that has been previously linked to the functional quiescence that characterizes the LG in SjS. Since cathepsins have collagenase/elastinase activity, the presence of both CATS and CATH in macrophages and other interstitial cells may also degrade tissue extracellular matrix, thus expediting the infiltration of immune cells and the loss of secreting function. Targeting CATS and CATH may therefore constitute alternative therapeutic strategies in the treatment of chronic autoimmune dacryoadenitis associated with SjS.

In summary, the NOD mouse model is an established model of SjS-like chronic autoimmune dacryoadenitis. Specific cathepsin family members and cytokines are upregulated during development and progression of disease in this mouse model, with a profile comparable to those changes seen in obesity, suggesting that the lipid deposition plays a causal role in the autoimmune inflammatory response. The profile of increased cathepsin protease expression and distribution within macrophages, other APCs and even within acinar cells suggest a complex role for these proteases in initiation and progression of autoimmunity. Overexpressed CATS secreted into the tear fluid from NOD mice reflects the initiation of disease and the consequent changes in LG function and thus may serve as a biomarker for diagnosis of autoimmune dacryoadenitis in human. CATS and CATH may also be considered as potential targets for alternative therapeutic approaches to treat and prevent progression of SjS, particularly if ways can be identified to specifically target such inhibitors to the sites of interest within the LG.

Experiment 2

SjS biomarkers in tears are correlated with the severity of inflammatory autoimmune lacrimal gland disease. Applicants can utilize three unique tear biomarkers for SjS, CtsS, Apo-F and Lcn-2, that can be expressed in tears at levels proportional to the extent of inflammatory autoimmune LG disease manifested in the source of the tears. In mouse and human tears, levels of these three biomarkers are quantified, and submitted to be increased in disease, in parallel with three tear secretory proteins, lactoferrin, lactoperoxidase and lysozyme, submitted to be generally decreased in SjS as well as other KCS disorders.

The NOD mouse and the IL1-injected BALB/c mouse represent two models of inflammatory autoimmune LG disease. Tears and ocular tissue samples are collected from these models at intervals relevant to disease development and progression. In parallel, the extent of inflammatory autoimmune LG disease is quantified by analysis of cornea, conjunctiva and LG. All biomarkers can additionally be screened in tears from populations of control and primary SjS patients with established clinical symptoms. Analysis of biomarkers in tears can use standard Western blotting, ELISA or biochemical tests.

Sjs Patients.

Patients with diagnosed primary SjS, according to the revised version of the European criteria proposed by the American-European Consensus Group, will be recruited from the USC Cornea Clinic, Rheumatology Clinic or LAC+USC with the aid of collaborating physicians. Since the majority of our SjS patients do not produce sufficient tears, these may require an "eye-wash". Before tear collection, SjS patients (and controls) will undergo a thorough eye exam. This information can be used for correlation studies. Briefly, a drop of local anesthetic (to collect unstimulated or basal tears) is first applied to the ocular surface followed by 2 drops of saline (because most SjS patients have no visible tears). To be consistent, tears should be collected from control subjects following the same protocol. The subjects are subjected to a Schirmer's test and test strips will be saved for collection of disease biomarkers. Tears are eluted into assay buffers for biochemical measurement of enzyme activity and/or analysis of protein content by bioassay or Western blotting. This method of collection has yielded tears from a variety of patients can be eluted for biochemical studies including resolution of proteins on SDS-PAGE gels (FIG. 10) and that exhibit a wide variation in Cathepsin S activity that appears to be related to disease state.

Figure 8:
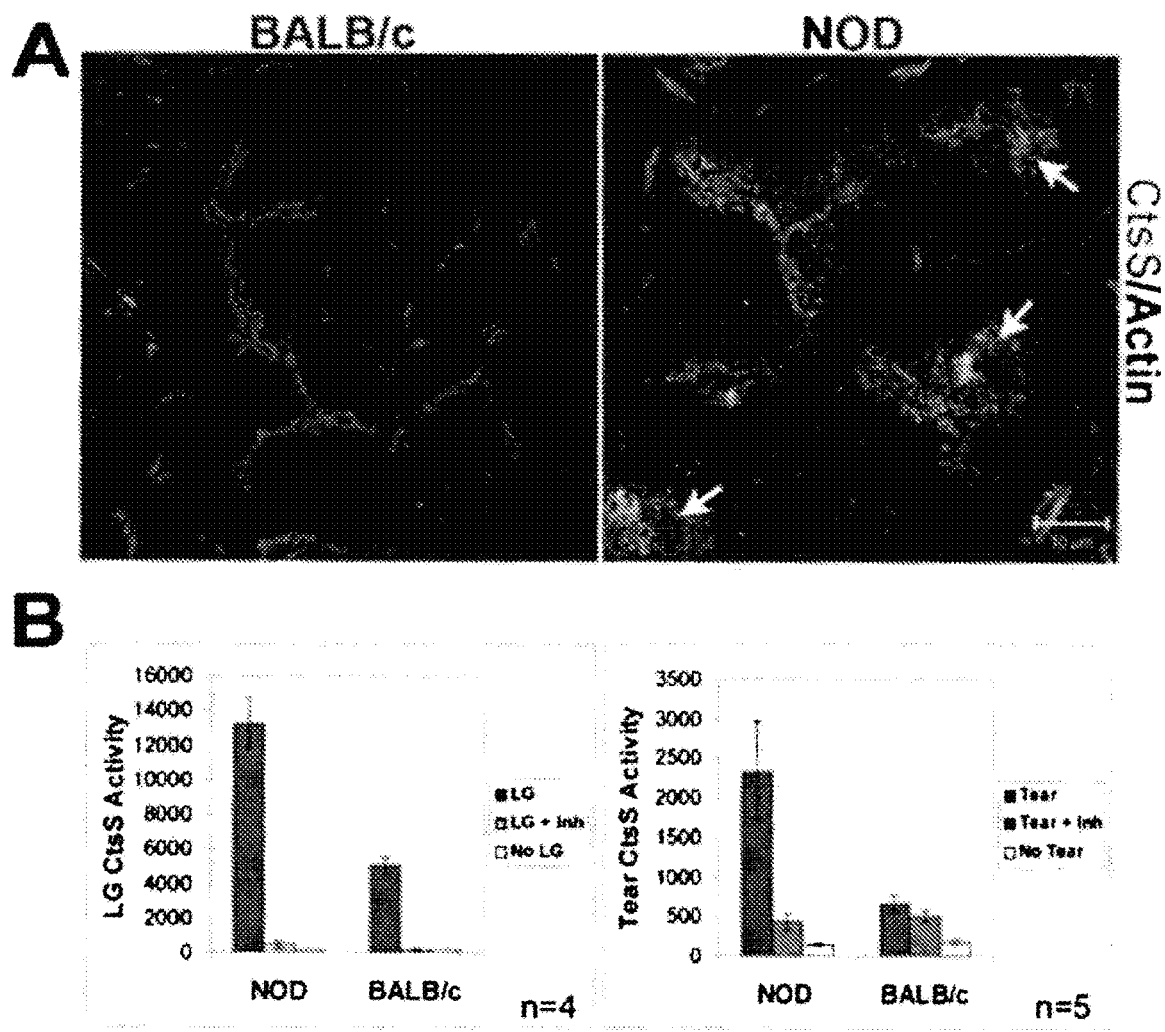
FIG. 8A shows that CtsS immunofluorescence is increased in male NOD mouse LG, particularly in large SV (arrows); actin, red; bar, 10 µm.
FIG. 8B shows CtsS activity in LG lysates and tears from 12 wk mice shows a significant ($p<0.05$) increase in male NOD mice. Inhibitor co-incubations show most activity is inhibited, verifying it is CtsS.

Potential Sjs Biomarkers to be Analyzed in Tear Fluid—Predicted Increase Associated With Disease CtsS is a type of cathepsin, a major class of lysosomal proteases. They are established effectors of protein degradation within the lysosomes, and their activity is critical to additional activities including precursor protein activation, MHC II-mediated antigen presentation, reproduction and apoptosis (Turk, et al. (2001) EMBO J. 20(17):4629-33). Several cathepsins are expressed in LG, but CtsS in particular has a compelling history related to autoimmunity. CtsS is highly expressed in antigen-presenting cells and is implicated in MHC II-mediated antigen presentation. It is implicated in the pathogenesis of degenerative immune diseases including chronic inflammation and rheumatoid arthritis. CtsS is also upregulated in response to lipid deposition, a feature of LG pathology strongly associated with inflammatory autoimmune disease in the NOD mouse LG. CtsS activity has been targeted therapeutically in a mouse model of SjS; SG and LG lymphocytic infiltration was prevented by prior administration of a CtsS inhibitor to SG. Significantly increased activity of CtsS in LG sections and tears from diseased male NOD mice is demonstrated. CtsS also shows an 11-fold increase in gene expression in male NOD mouse LG, relative to age-matched BALB/c mouse LG. The biochemical spectrophometric assay illustrated in FIG. 8B can be utilized for measurements of CtsS activity in tears.

Apo-F is a constituent of HDL and LDL, and can be associated with cholesterol and cholesterol esters in lipoproteins. Very little is known about its biological function. Recent findings in the LG suggest that it may normally modulate cholesterol influx and/or excretion in LG at the basolateral membrane, and that its extensive upregulation, possibly in response to metabolic abnormalities and/or inflammation in diseased LGAC, may lead to its mis-sorting and apical excretion into tears. Apo-F shows an 53-fold increase in gene expression in male NOD mouse LG, relative to age-matched BALB/c mouse LG, and its content in male NOD mouse tears is markedly increased relative to virtually undetectable levels in tears from age-matched BALB/c controls. Its presence and abundance in tears will be quantified by Western blotting in these proposed studies. To supplement mouse-specific Apo-F antibody, which can be used to probe mouse tears in healthy and diseased mice, a human-specific Apo-F antibody can be utilized. Applicants have obtained such from Drs. Bill Lagor and Daniel Rador (University of Pennsylvania) that is appropriate for immunoblotting of human tears from healthy and primary SjS patients.

Figure 9:
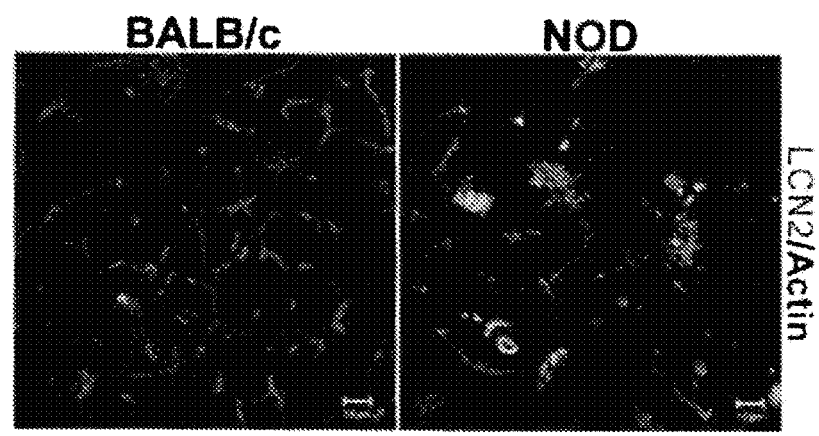
FIG. 9 shows that Lcn-2 immunofluorescence is detected at increased intensity at the basolateral membranes as well as adjacent to or inside lumenal regions in the 12 week male NOD mouse LG relative to age-matched BALB/c mouse LG. Actin filaments, and nuclei. Bar, 10 µm.

Lcn-2, also called neutrophil gelatinase-associated lipocalin, is expressed in both mice and humans, and has been shown to be highly expressed in pancreatic islets, bone marrow, and SG. Until now its expression in LG has not been investigated but microarray data suggest moderate to high levels of expression. It is implicated in diverse bioprocesses including iron-siderophore binding in bacterial infections as a component of the innate immune system, modulation of inflammation, and is a marker closely related to obesity and insulin resistance (Flo, et al. (2004) Nature 432(7019):917-21, 13). FIG. 9 shows the apparent increase in the immunofluorescence associated with Lcn-2 in diseased male NOD mouse LG and its redistribution to mature secretory vesicles and within the lumena, suggesting drainage into tears. These observations, in parallel with the 2.4× upregulation of Lcn-2 in diseased NOD mouse LG relative to BALB/c mouse LG, suggests its utility as a putative tear biomarker. Like CtsS, its upregulation in diseased NOD mouse LG may be related to tissue lipid deposition which characterizes this animal model as well as SjS patients. Lcn-2 has also been reported to be upregulated under conditions of inflammation and by IL-1β and IFNγ cytokines. Applicants have had difficulty reliably detecting a signal for Lcn-2 by Western blotting in tears of NOD mice, likely due to relative antibody insensitivity. This is one of the reasons that this biomarker was chosen for development of an ELISA capture assay in as discussed above, as well as the more sensitive cyclotide-based assay also discussed above.

Potential Sjs Biomarkers to be Analyzed in Tear Fluid-Predicted Decrease Associated With Disease Lactoperoxidase, Lactoperoxidase is a secreted glycoprotein member of the peroxidase family. It has antimicrobial properties due to its ability to sequester calcium, iron and heme B, and also supplies a potent antioxidant activity to the tears through its ability to form reactive bromine and iodine species through hydrogen peroxide oxidation of halides (Ghibaudi & E. Laurenti (2003) Eur J. Biochem. 270(22): 4403-12). Its activity can be measured through simple spectrophotometric assays.

Lactoferrin, is also a secretory glycoprotein that is a member of the transferrin family. It is the principal iron-binding protein in milk and bodily secretions, providing a potent antimicrobial activity as part of the non-specific immune system. It has a broad range of activity including regulation of iron homeostasis, host defense, regulation of growth and differentiation and protection against cell transformation (Weinberg (2007) Curr Pharm Des. 13(8):801-11; Zimecki et al. (2007) J. Exp Ther. Oncol. 6(2):89-106). It can be assayed by ELISA using commercially available antibodies, or immuno-immobilization followed by enzymatic activity assays using commercially available kits.

Lysozyme, is a secretory protein that is ubiquitously present in human serum, urine, tears and milk (Zimecki et al. (2007) J. Exp Ther. Oncol. 6(2):89-106). It hydrolyzes glycosyl linkages present in the mucopolysaccharide cell wall of diverse organisms. It can be assayed using a simple fluorescence-based enzymatic activity assay that is commercially available.

Collection and Analysis of Tissues and Fluids:

In mouse models, a comprehensive series of established assays can be conducted to quantify the extent of disease development and progression including an analysis of tear flow and corneal integrity in the live animal, as well as the isolation and analysis of tissue integrity and inflammation in LG, cornea and conjunctiva after tear collection and sacrifice of the animal. The relationship between the basic assays that will be conducted and the designation of autoimmune inflammatory disease development in mouse models as mild, moderate or severe is shown in Table 1.

Tear Flow and Corneal Integrity in Live Mice:

For measurement of tear production and corneal integrity in live mice, one means is cotton threads pre-impregnated with phenol red that turn red upon contact with tear fluid. Mice can be anesthetized with 2-3% isoflurane. The thread is inserted into the lateral canthus for 30 sec with care not to touch the cornea. Wetting of the thread is evaluated under the magnifier by at least 2 evaluators and averaged in millimeters. After the measurement with the cotton thread or in separate populations of anesthetized mice, corneas are evaluated for any pathological signs as reflected by fluorescein staining in a dark room. One μL of freshly made 1% sodium fluorescein is carefully applied to the lateral canthus and the eyelids manually blinked 3× to spread the solution. Excess solution is removed by gently applying a Kimwipe tissue to the lateral canthus and corneal fluorescein staining is immediately (within 30 sec of addition) evaluated and photographed with a Motic microscope equipped with a CCD camera using a cobalt blue light. Images are evaluated and graded by a standard protocol. These tests can be conducted on the same mice that will subsequently be used for collection of tear fluid, LG and ocular surface tissue below, as long as the mice are allowed to recover from anesthesia for several hrs following the isoflurane.

Analysis of Biomarker Content of Tear Fluid:

For collection of lacrimal fluid, mice are anesthetized with ketamine/xylazine, placed on a heated surgical table and immobilized with non-penetrating steel pins. One LG is exposed. The duct and gland is freed via blunt dissection and care is taken not to injure nearby nerves and blood vessels. The thin connective tissue capsule enclosing the gland is carefully opened and removed. To limit the spread of the superfusate, the LG is covered with a Kimwipe mesh. Fluid is drained from the mesh with a rigid aspiration pipette. Drugs and chemicals are added to the superfusate with a wash-in time of ~30 seconds. A microcapillary tube is placed near the lacrimal duct to collect basal and stimulated tear fluid. After fluid from one gland has been collected the other gland is similarly exposed for collection of tear fluid.

A mouse typically yields about 1 μL of tear fluid, varying according to the age, gender and extent of disease development. All biomarkers in pooled mouse tear samples, from 5 mice per experimental data point, are analyzed. At least 5 separate assays points are obtained from pooled specimens under each disease condition or time point. Assays will vary according to the biomarker under study. For CtsS, lactoperoxidase, and lysozyme one can measure enzymatic activity while for Apo-F, Lcn-2 and lactoferrin, one can use either Western blotting or ELISA. For Lcn-2 measurement can also use the cyclotide-based assay described in previous paragraphs.

Analysis of Ocular Surface and LG Disease:

At the conclusion of the tear collection, eyeballs and LG are isolated and either flash frozen or paraffin-embedded according to standard methods to obtain tissue sections for immunofluorescence microscopy or histology. Sections from LG are stained with hematoxylin and eosin to evaluate cytoarchitecture and to assess lymphocytic infiltration. If evidence for lymphocytic infiltration is seen, extent of lymphocytic infiltration are quantified per unit area of LG and the identify of infiltrating cells (T cells, B cells, macrophages) are further assessed using indirect immunofluorescence of frozen sections and appropriate commercial primary and secondary antibodies. One can also isolate whole LG and measure levels of inflammatory cytokines using RT-PCR as evidence of inflammatory disease. Corneal and conjunctival sections from control and disease model mice are processed with Movat's pentachrome stain or Periodic-Schiff's reagent to detect loss of goblet cells and mucins and corneal stromal damage, both of which are established as markers for ocular surface damage (Dursun et al. (2002) Adv Exp Med. Biol. 506(Pt A):647-55). The same sections can be analyzed by hematoxylin and eosin staining to evaluate possible lymphocytic infiltration, and if seen, the composition of the infiltrates can be analyzed by indirect immunofluorescence as above.

Measurement of Biomarkers in Tears and LG:

Activity (CtsS, Lactoperoxidase, Lysozyme) or protein content (Apo-F, lactoferrin, Lcn-2) can be measured as described for each protein in the preceding biomarkers section, and signal normalized both to tear volume collected as well as total tear protein. This latter calculation is particularly important since in some of the primary SjS patients, tears may need to be collected by gentle washing of the ocular surface because of the complete loss of fluid flow. To understand how changes in tear composition may be due to disease-specific changes in gene expression of the proteins, one can conduct real-time PCR analysis of the relative mRNA content for each protein. This will help in determining the most specific biomarkers that are most directly associated with severe inflammatory disease.

Interpretation and Challenges

Applicants predict that the abundance of each of the disease-induced biomarkers (CtsS, Apo-F and Lcn-2) in tears from control animals will be minimal, and that their content in the tears will increase in proportion to the severity of autoimmune inflammatory disease in the mouse models. It has never been explored whether the expression of these biomarkers increases as disease progresses in the NOD mouse, beyond the 4-12 week time-points measured so far at disease onset. It has also never been explored whether these biomarkers are secreted into tears in any other mouse model of disease. These potential novel biomarkers are newly discovered and have also never been comparatively measured in healthy and primary SjS patient tears. The parallel measurement of gene expression using real-time PCR will aid Applicants in identifying markers that are uniquely upregulated and secreted to tears in inflammatory autoimmune disease. Such an increase over a low background or threshold would be ideal for translational development as a biomarker of disease.

Experiment 3

Purpose:

Previous work has revealed age- and inflammatory disease-correlated alterations in apolipoproteins F (Apo-F) and E (Apo-E) in mouse lacrimal gland (LG) along with abnormal lipid deposition. The current experiment characterizes the expression and distribution of apolipoproteins in human LG in comparison to healthy (BALB/c) and Sjögren's syndrome disease model (NOD) mouse LG.

Methods:

Microarray was conducted with RNAs prepared from two human male LG groups, young (54 years average) and old (77 years average) (n=3 per group), and data compared using Partek GS software (Parteck Inc. St. Louis, Mo.). Cryosections of LGs from humans of both genders and mouse models were evaluated microscopically using immunofluorescence and Oil Red O.

Results:

Microarray analysis detected expression of the following genes in human LG: APO-C1, APO-D, APO-E and APO-F. In older males, APO-C1, APO-D and APO-E genes were moderately upregulated to 2.6, 1.5 and 1.3 folds while APO-F was downregulated to 60% relative to the younger group (p<0.02). Apo-E protein was universally detected at the basolateral membrane of acinar cells from different specimens. However, Apo-F protein distribution varied markedly in acinar cells. Apo-F was observed in some human LGs at the cytoplasmic face of the plasma membrane but beneath basolateral ApoE, rather than the co-localization of the two proteins seen in BALB/c mouse acinar cells. ApoF in acinar cells from other human LG was detected in a dispersed distribution within cytoplasmic and secretory vesicle-like organelles comparable to the pattern in NOD mouse LG. Without being bound by theory, this finding indicates that similar to mouse, human individuals in which Apo-F is dispersedly distributed within cyoplasmic and secretory vesicle-like organelles are likely suffering from Sjögren's syndrome or at risk of developing Sjögren's syndrome, whereas human individuals in which Apo-F is located at the cytoplasmic face of the plasma membrane in the acinar cells are likely not suffering from Sjögren's syndrome or at risk of developing Sjögren's syndrome. The dispersed distribution of ApoF in NOD mouse LG and certain human LG is believed to result from missorting of ApoF in the acinar cells. Finally, Oil Red O staining showed many adipocytes scattered within human LG but not within mouse LG.

Conclusion:

The detection of adipocytes and several apolipoprotein mRNAs indicates that the human LG is active in lipid metabolism. Apo-F is subject to age-related regulation and its cellular location appears highly variable in human LG, suggesting the possibility of alterations under pathological conditions. This finding further indicates that, the disparate distribution patterns of missorted proteins, such as Apo-F as well as CATS as observed in the NOD mouse model compared to healthy mice, are promising markers for the diagnosis of Sjögren's syndrome, not only in mouse, but also in human and other mammals. Accordingly, the presence of Apo-F or CATS at the cytoplasmic face of the plasma membrane in acinar cells in a LG from a mammal indicates that the mammal is not likely suffering from Sjögren's syndrome or is at risk of developing Sjögren's syndrome. A dispersed distribution of Apo-F or CATS within cytoplasmic or secretory vesicle-like organelles in acinar cells in a LG from a mammal indicates that the mammal is suffering from Sjögren's syndrome or is at risk of developing Sjögren's syndrome.

Experiment 4

This experiment was designed to determine the range of activity levels of cathepsin S in normal and diseased human tears using a simple, accessible assay based on the Schirmer's test that is available to the non-specialist. Meanwhile, the experiment determines if increased cathepsin S activity per unit protein in tears is correlated with diagnosed Sjögren's syndrome, so that it may function as a diagnostic biomarker.

A Schirmer's test, which measures tear flow, is a routine part of the intake process for all new patients and for the continuing evaluation of patients with ocular surface disorders. Classification for a Schirmer's test is as follows. A Schirmer's value 0-5 mm indicates severe dry eye, 5.1-10 mm indicates moderate dry eye, 10.1-15 mm indicates mild dry eye, and >15 mm indicates normal tear flow.

All patients receiving Schirmer's tests by the participating physicians were given an informed consent form and a small recognition for participation.

Fifty-three patients (106 eyes) were tested (all-corners trial) from patients accrued at the USC/Doheny Ophthalmology Clinic. Schirmer's strips, which measure unstimulated wetting of the anesthetized eye over 5 min, were collected and stored for up to 4 hours at 4° C. Human cathepsin S catalytic activity eluted from Schirmer's strips does not change within this window. Assays are conducted blinded (samples were labeled with regards to left or right eye). The proteins are eluted from Schirmer's strips and assayed for cathepsin S activity and for protein content.

Patient gender and disease status are then provided and matched to the activity assay values for analysis of general trends.

Figure 10A:
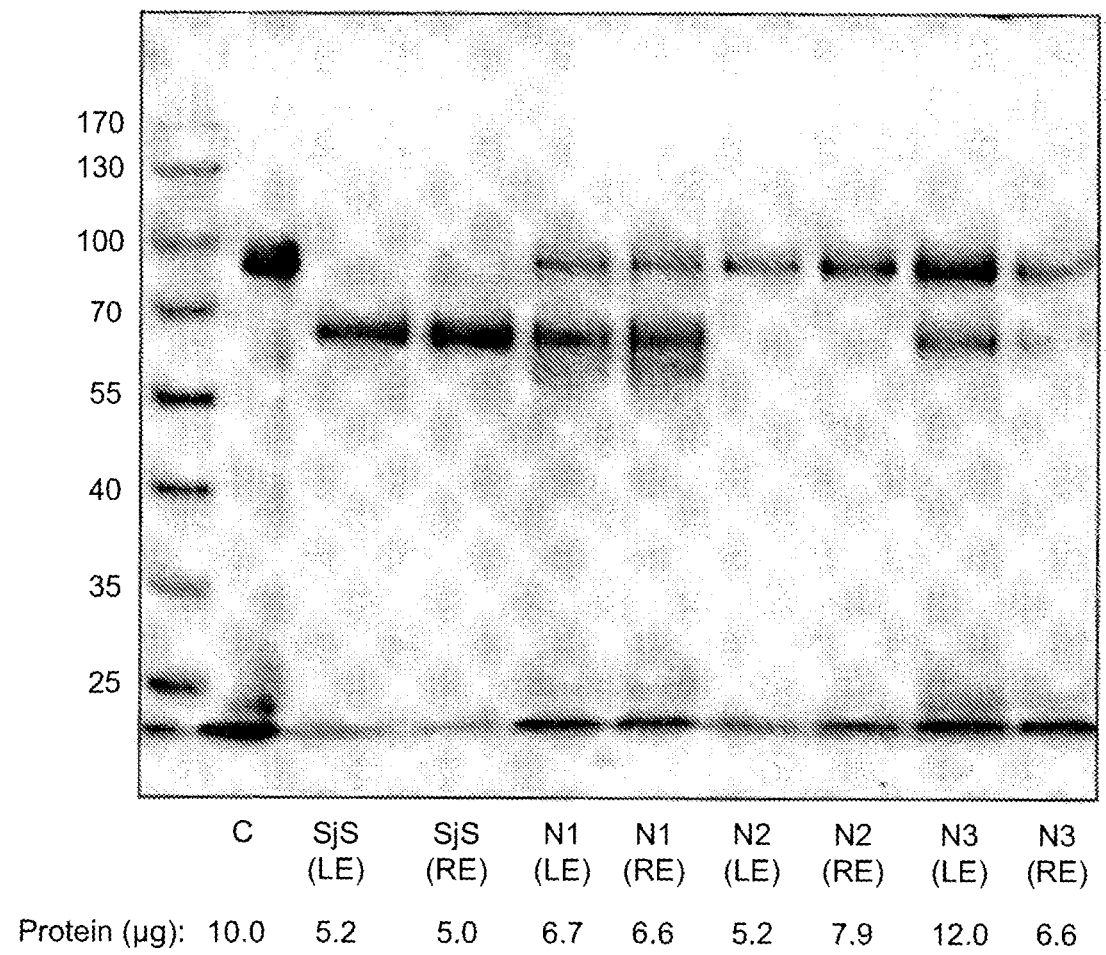
In FIG. 10A, human tear proteins were separated by SDS-PAGE after being processed through cathepsin S assay. Protein was run on a 1.5 mm thick 10% gel and stained with GelCode Blue Stain Reagent (Pierce). C=fresh tears, SjS=Sjogren's patient, N=normal patients. LE=left eye, RE=right eye. Molecular weight markers are in kDa. Max protein was loaded per lane, so amounts are varying as labeled.
Figure 10B:
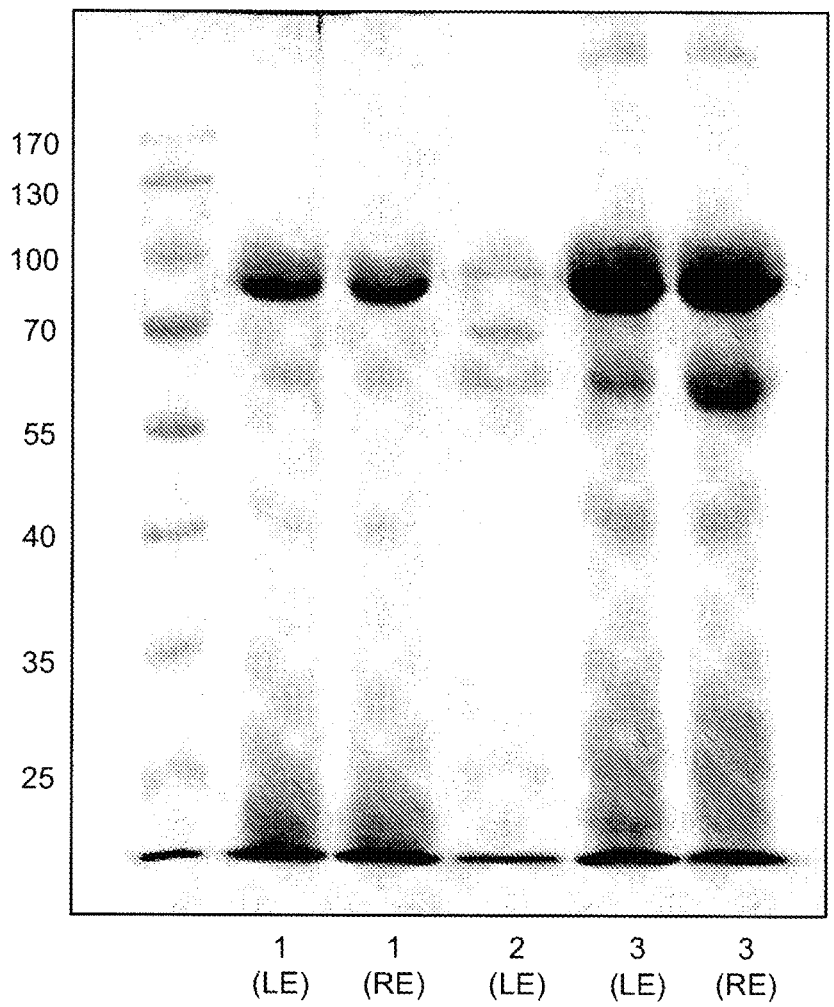
In FIG. 10B, fresh human tears (33 mg, each lane) were separated by SDS-PAGE on a 0.75 mm thick 10% gel and stained with GelCode Blue Stain Reagent (Pierce). Patient 2 was a SjS patient. Patients 1 and 3 were normal patients with no disease. LE=left eye, RE=right eye. Molecular weight markers are in kDa.
Figure 11:
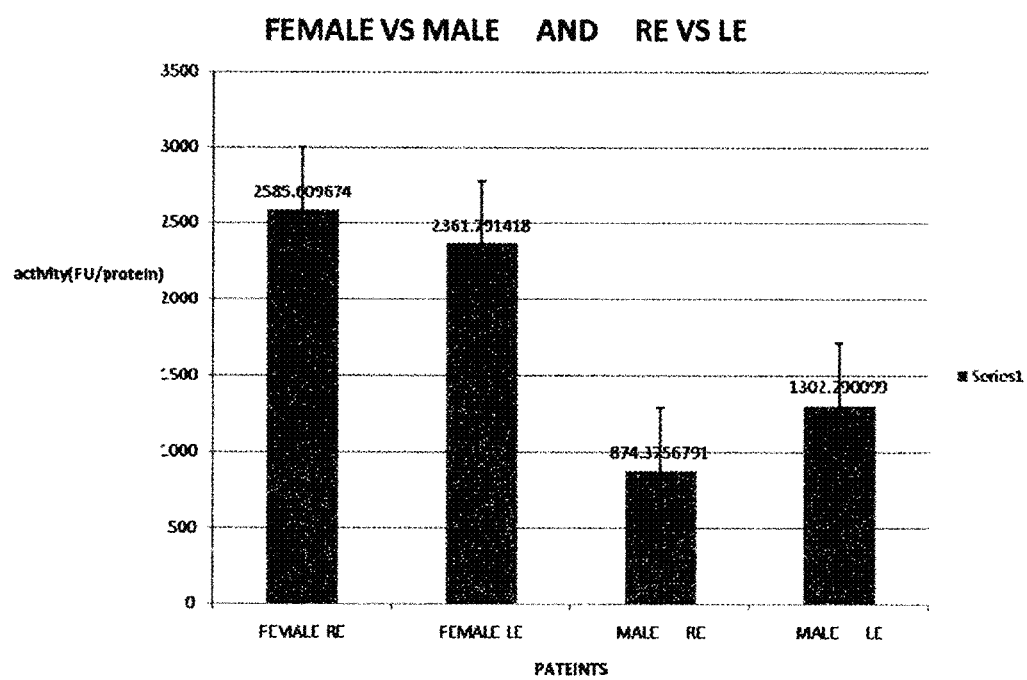
FIG. 11 is a bar chart showing differences of activity levels of cathepsin S in human tears collected by modification of the Schirmer's test protocol onto filter paper strips followed by elution and measurement of CatS activity and protein. Values vary between genders. RE: right eye. LE: left eye.

As shown in FIG. 10, female patients tend to have higher CATS activities than male. FIG. 11 shows that a number of patients showed drastically increased CATS activities. Surprisingly, two of the three patients with the highest CATS activities were diagnosed with Sjögren's syndrome and lupus.

Figure 12:
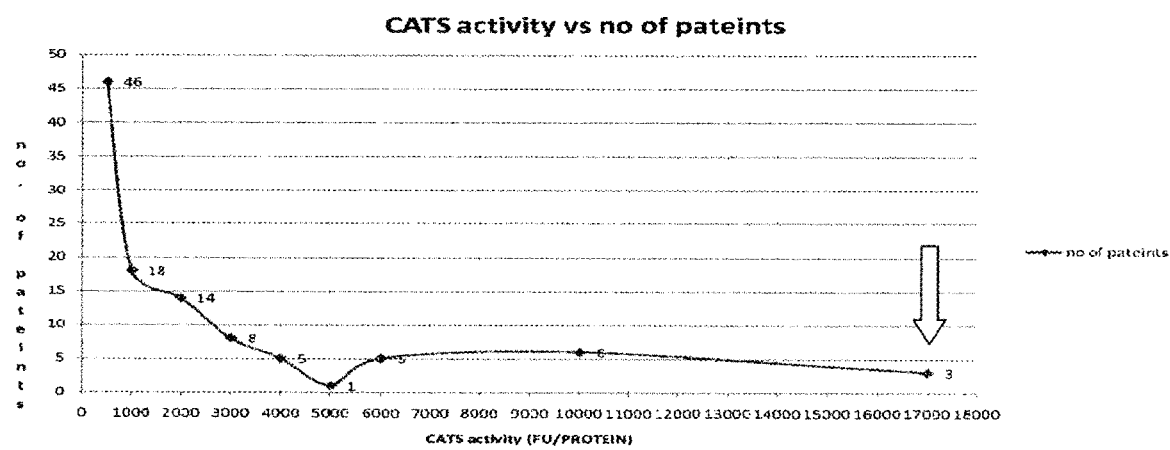
FIG. 12 is a distribution curve showing that two of the three patients with the highest cathepsin S activities in a set of clinical samples plotted by eye were diagnosed with Sjögren's syndrome or lupus (indicated by the arrow).

FIG. 12 shows that high CATS activity correlated with SjS and lupus conditions (CATS activity for the diagnosed patients<11831). It is worth noting that other patients exhibiting high CATS/protein activity may have undiagnosed SjS/lupus.

Figure 13:
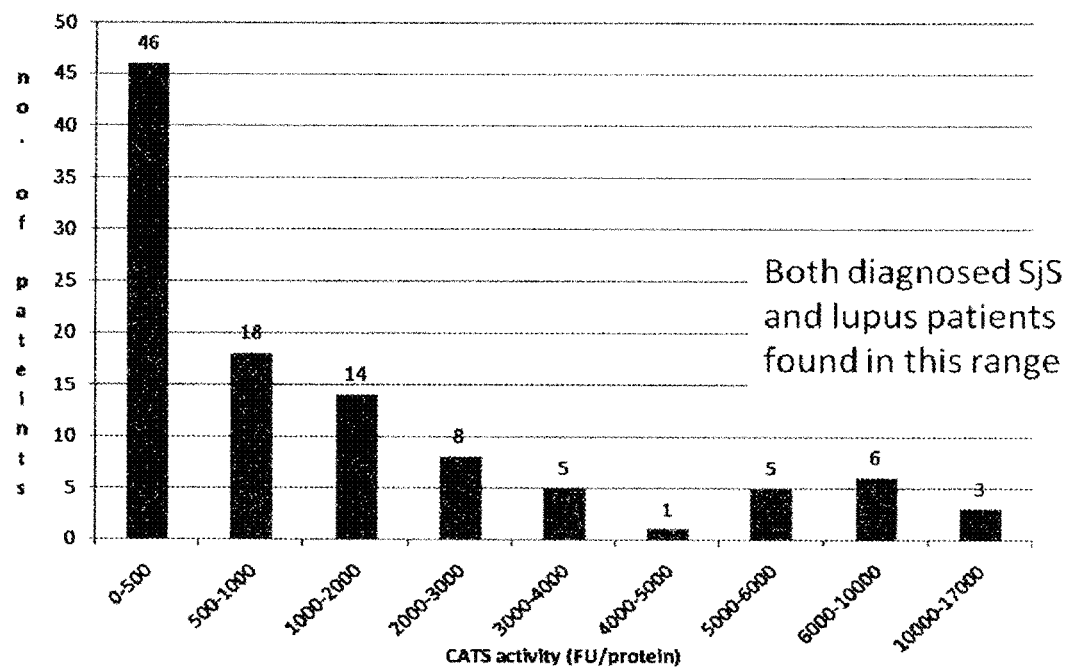
FIG. 13 is a distribution bar chart showing that patients with Sjögren's syndrome or lupus were among the patients with the highest cathepsin S activities.
Figure 14:
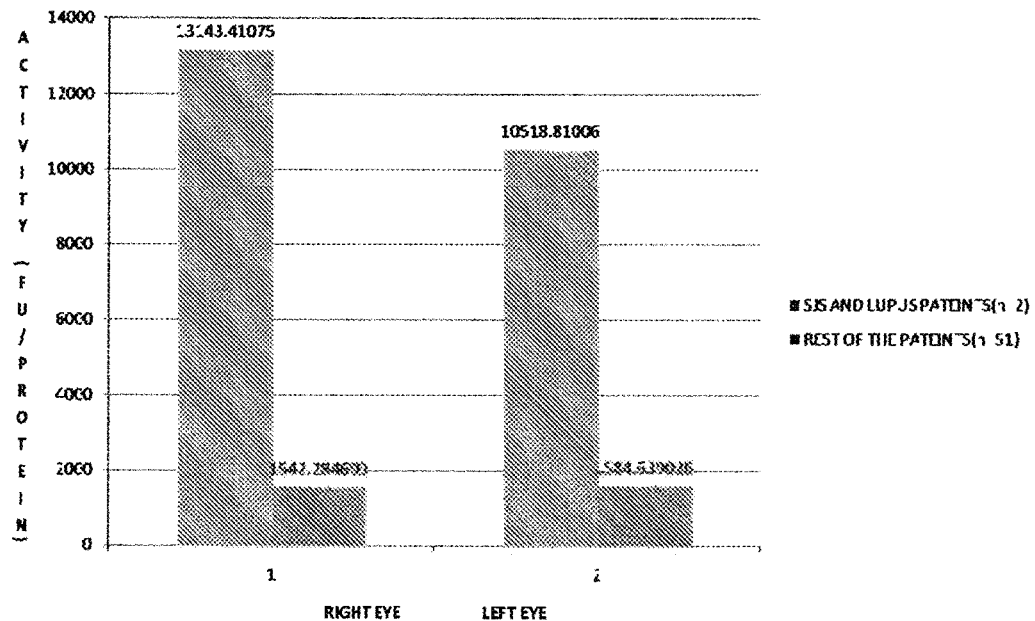
FIG. 14 shows that compared to other patients, cathepsin S activity levels in Sjögren's syndrome or lupus patients were much higher.
Figure 15:
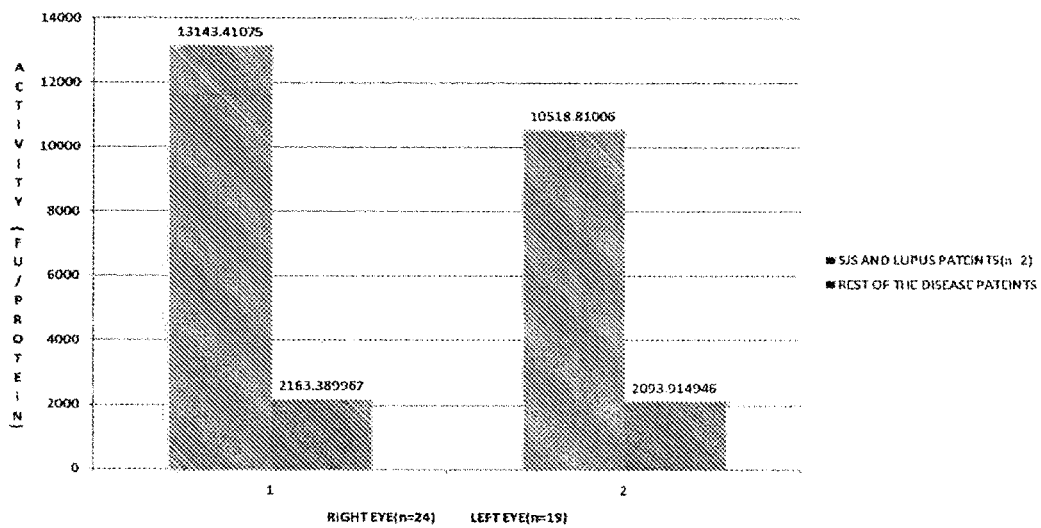
FIG. 15 shows that compared to patients with other diseases, cathepsin S activity levels in Sjögren's syndrome or lupus patients were much higher.
Figure 16:
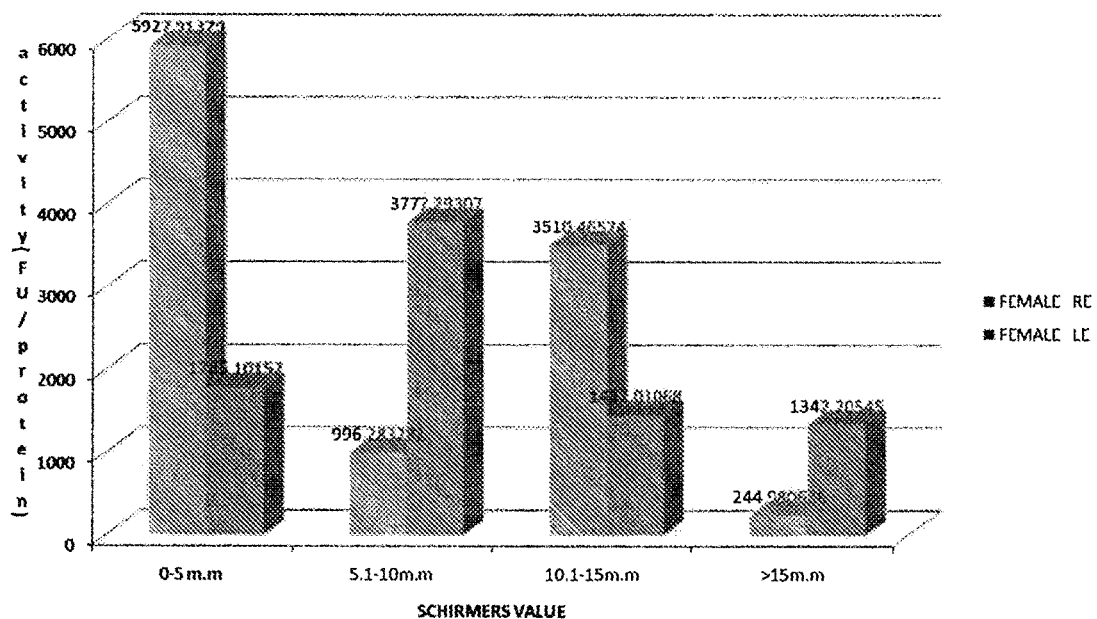
FIG. 16 shows in female patients, CATS activities are the highest in patients with the lowest Schirmer's values.
Figure 17:
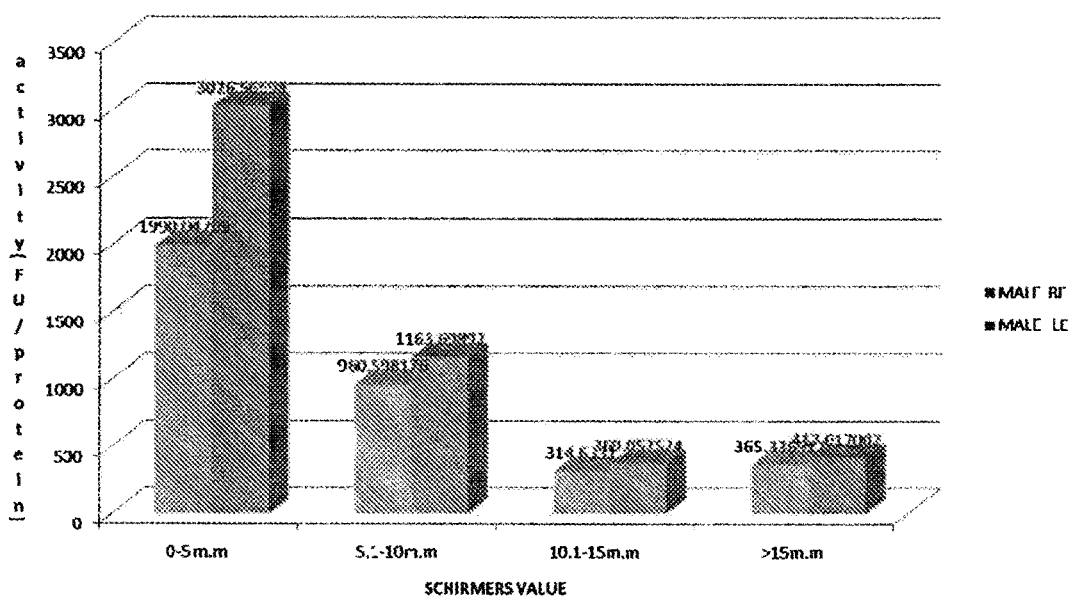
FIG. 17 shows in male patients, CATS activities are the highest in patients with the lowest Schirmer's values.
Figure 18:
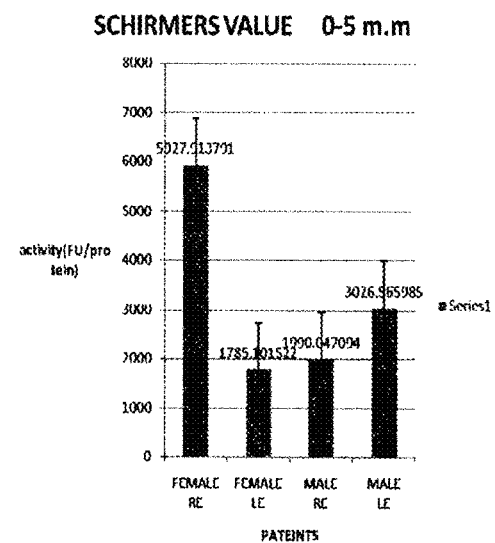
FIGS. 18-21 show in patient groups of different ranges of Schirmer's values, the CATS activities among female and male patients.
Figure 19:
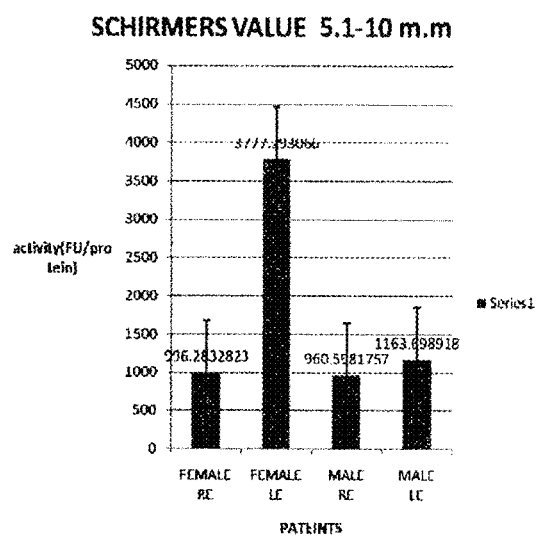
Figure 20:
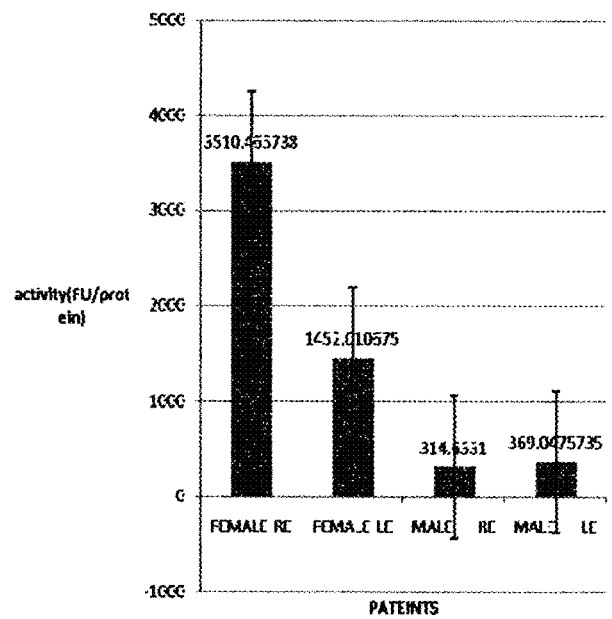
Figure 21:
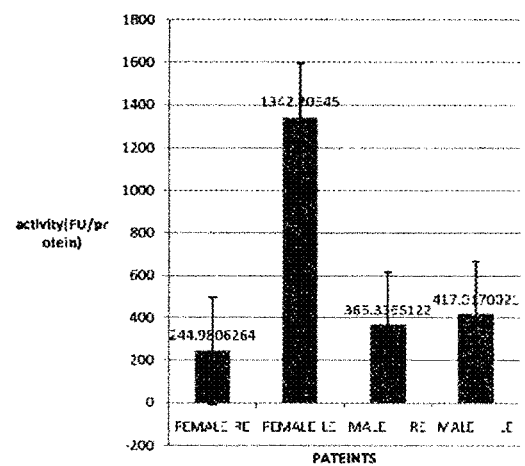
Figure 22:
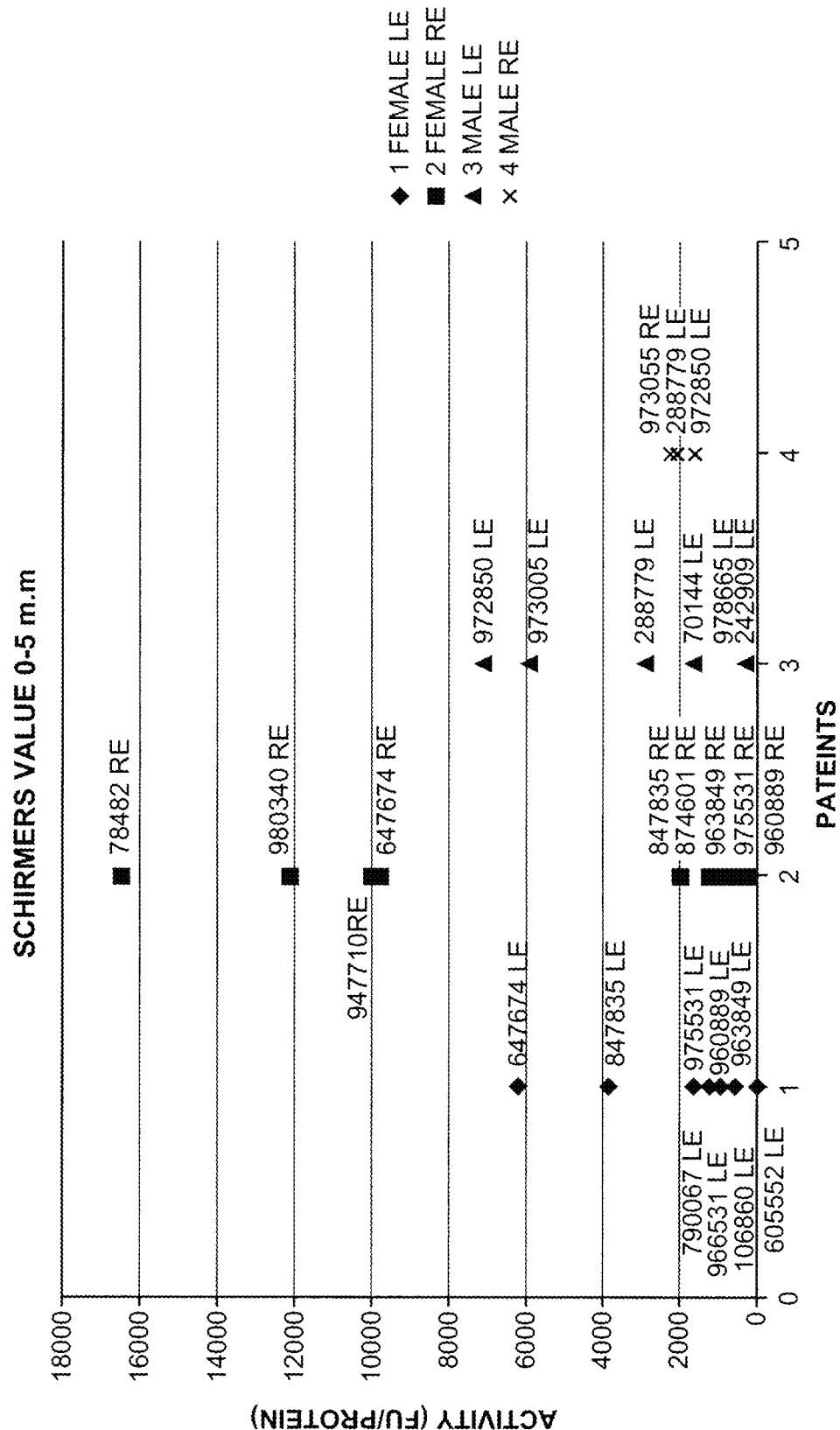
FIGS. 22-25 show in patient groups of different ranges of Schirmer's values, the CATS activity values of specific patients.
Figure 23:
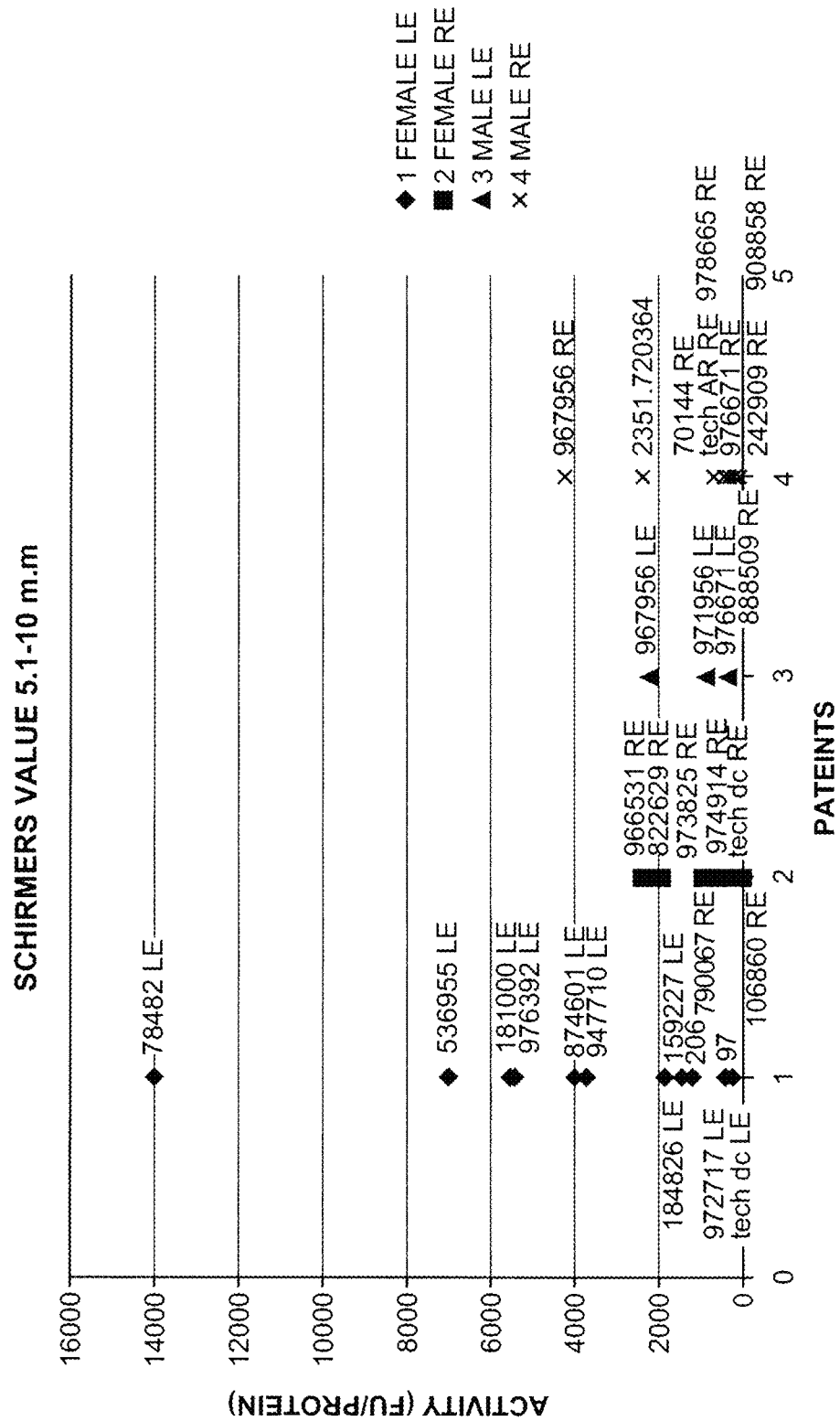
Figure 24:
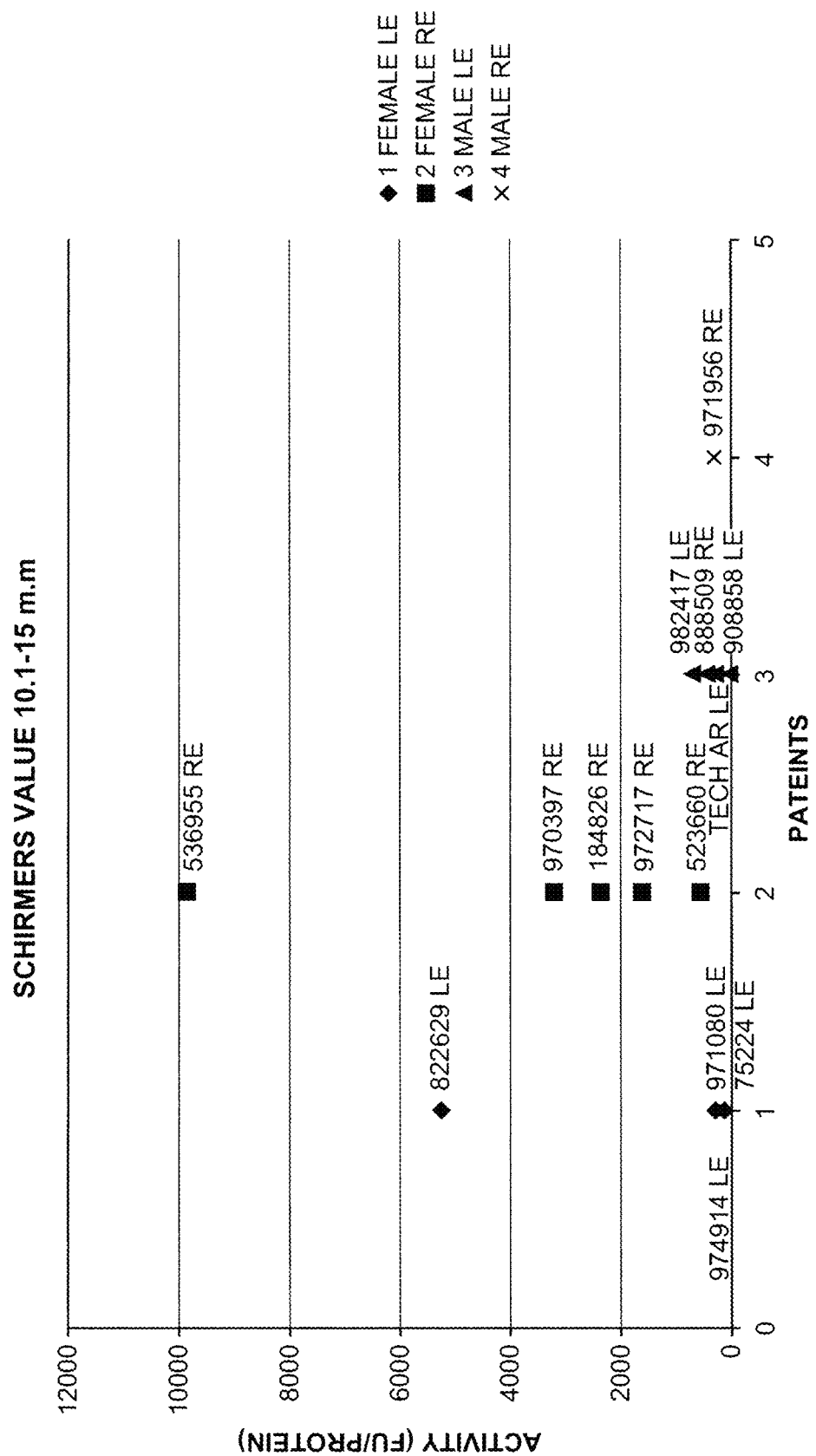

Further, FIGS. 13 and 14 show bar charts indicating that the CATS captivities in SjS and lupus patients were significantly higher than other patients or patients with other diseases.

Figure 25:
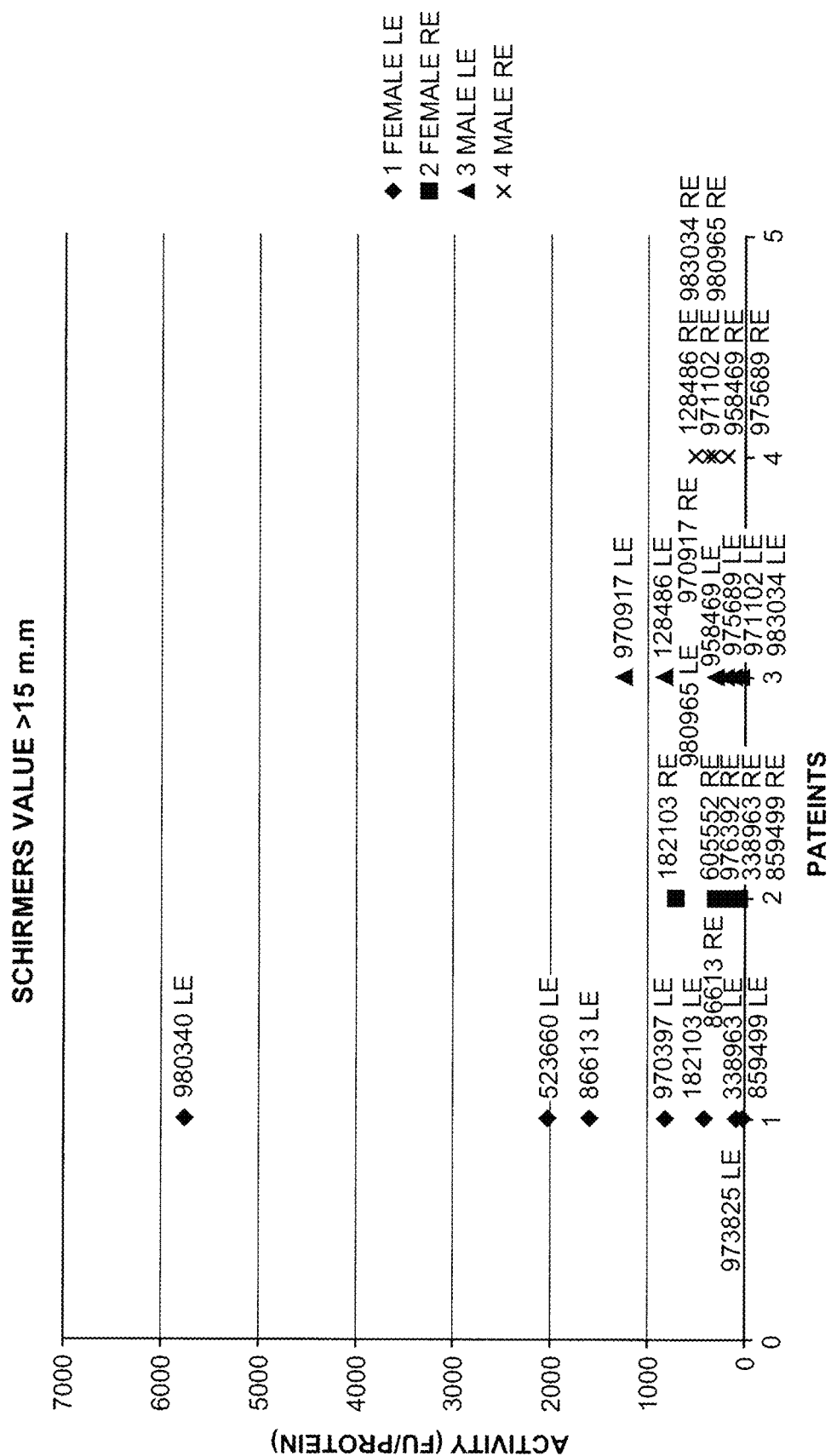
Figure 26:
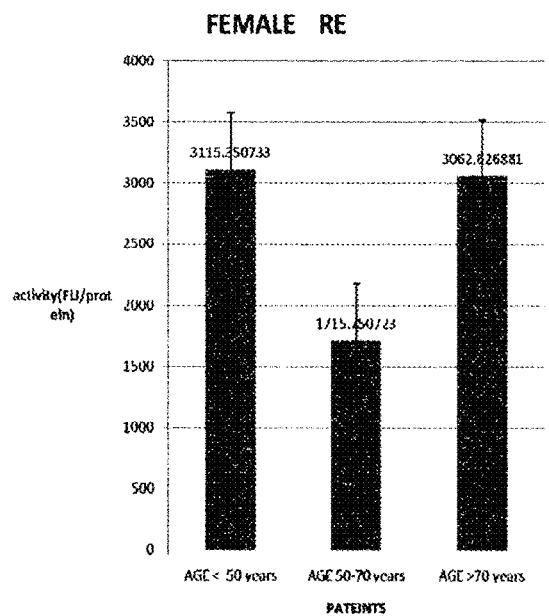
FIGS. 26-29 show the CATS activities of female or male patients in different age groups.
Figure 27:
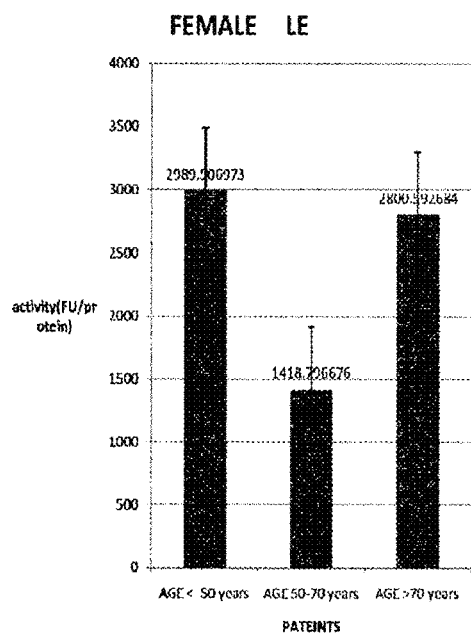
Figure 28:
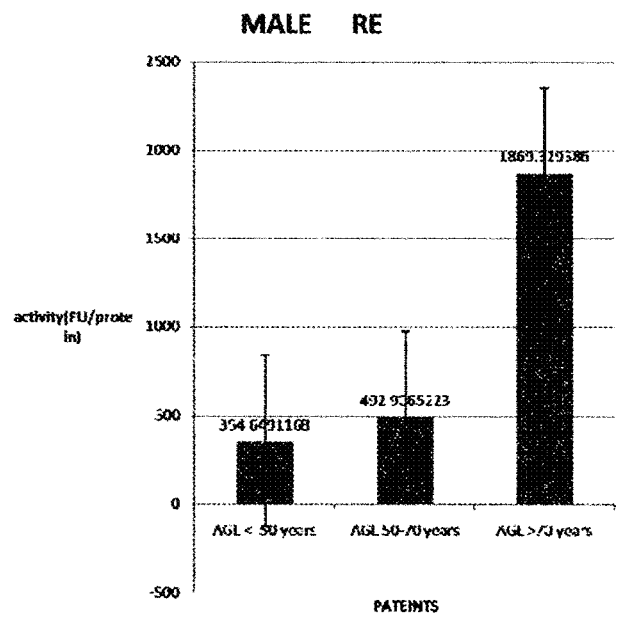
Figure 29:
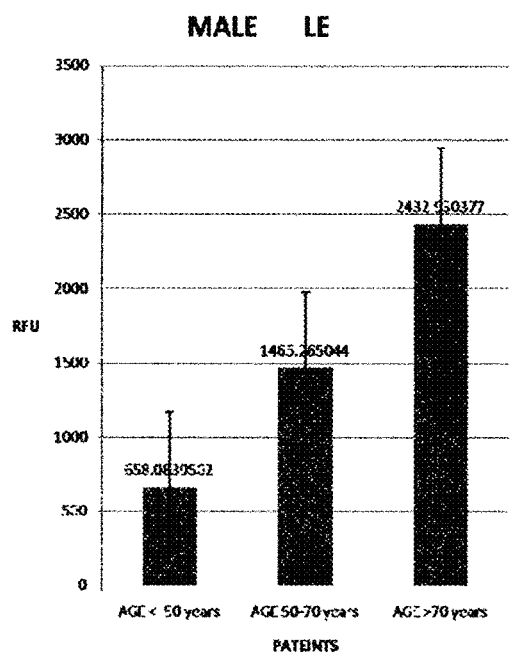

It was further observed that patients with lower Schirmer's values generally had higher CATS activities (FIGS. 15-24) and older male patients generally had higher CATS activities (FIGS. 27-28). The age difference among female patients, however, was not observed (FIGS. 25-26).

Therefore, the current experiment shows that (1) female CtsS/protein in tears higher than in males; (2) in both males and females, CtsS/protein in tears is highest in patients with low Schirmer's scores; (3) the two patients with diagnosed SjS or lupus had the highest CtsS/protein activities.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A method for determining an expression level or activity level of cathepsin S (Ctss) in a mammal, the method comprising:
    contacting a tear sample collected on a filter substrate from the mammal with a quantitative fluorometric antibody or a quantifiable label contained or embedded within the filter substrate; and
    measuring the amount of antibody bound to Ctss to determine the expression level or activity level of Ctss in the tear sample.

2. The method of claim 1, further comprising measuring an expression level or an activity level of at least one additional polypeptide selected from the group consisting of cathepsin H (Ctsh), cathepsin R (Ctsr), cathepsin W (Ctsw), cathepsin Z (Ctsz), interferon gamma (Ifng), interleukin 10 (Il10), interleukin 10 receptor, alpha (Il10ra), interleukin 15 (Il15), tumor necrosis factor alpha (Tnfa), apolipoprotein F (Apo-F), and lipocalin 2 (Lcn-2); or a lactoperoxidase polypeptide in the tear sample using a quantitative fluorometric antibody contained or embedded within the filter substrate by measuring the antibody bound to the at least one additional polypeptide.

3. The method of claim 1 or 2, further comprising examining the mammal with one or more of a slit-lamp examination, a radiological test, or a blood test.

4. The method of any one of claim 1 or 2, wherein the mammal is a human patient.

5. The method of claim 1, further comprising determining the presence of a protein selected from CATS or APO-F in an acinar cell isolated from the lacrimal gland or salivary gland of the mammal.

6. The method of claim 5, wherein the protein is APO-F.

7. The method of claim 5, wherein the mammal is a human patient.

8. The method of claim 4, further comprising adjusting the measured level of Ctss for age or gender of the human patient.

9. The method of 8, wherein the filter substrate comprises a quantitative and detectably labeled substrate specific for Ctss.

10. The method of claim 9, wherein the quantitative detectably labeled substrate is a flourometrically labeled antibody.

11. The method of claim 2, further comprising eluting Ctss, the at least one additional polypeptide, or the lactoperoxidase polypeptide from the filter substrate and wherein the expression level of Ctss, the at least one additional polypeptide, or the lactoperoxidase polypeptide is measured by one or more method of the group of fluorometric analysis, Western blot, gel electrophoresis, ELISA, mass spectrometry, or protein array.

12. The method of claim 2, further comprising eluting Ctss, the at least one additional polypeptide, or the lactoperoxidase polypeptide from the filter substrate and wherein the activity level of Ctss, the at least one additional polypeptide or the lactoperoxidase polypeptide is measured by protease activity assay.

13. The method of claim 1, further comprising eluting Ctss from the filter substrate.

14. The method of claim 1, wherein the amount of antibody bound to Ctss is measured by one or more method of the group of fluorometric analysis, Western blot, gel electrophoresis, ELISA, mass spectrometry, or protein array.

15. The method of claim 1, wherein the activity level of Ctss is measured by protease activity assay.

* * * * *